United States Patent
Butler et al.

(10) Patent No.: US 7,183,408 B2
(45) Date of Patent: Feb. 27, 2007

(54) PROCESS FOR THE SYNTHESIS OF 5-(4-FLUOROPHENYL)-1-[2-((2R,4R)-4-HYDROXY-6-OXO-TETRAHYDRO-PYRAN-2-YL)-ETHYL]-2-ISOPROPYL-4-PHENYL-1$H$-PYRROLE-3-CARBOXYLIC ACID PHENYLAMIDE

(75) Inventors: Donald Eugene Butler, Holland, MI (US); Randall Lee DeJong, Zeeland, MI (US); Jade Douglas Nelson, Holland, MI (US); Michael Gerard Pamment, Holland, MI (US); Timothy Lee Stuk, Holland, MI (US)

(73) Assignee: Warner-Lambert Company, LLC, Morris Plains, NJ (US)

( * ) Notice: Subject to any disclaimer, the term of this patent is extended or adjusted under 35 U.S.C. 154(b) by 59 days.

(21) Appl. No.: 11/109,396

(22) Filed: Apr. 19, 2005

(65) Prior Publication Data

US 2005/0239869 A1 Oct. 27, 2005

Related U.S. Application Data

(62) Division of application No. 10/348,727, filed on Jan. 21, 2003, now Pat. No. 6,933,393, which is a division of application No. 10/198,682, filed on Jul. 18, 2002, now Pat. No. 6,545,153, which is a division of application No. 10/015,558, filed on Dec. 17, 2001, now Pat. No. 6,476,235.

(60) Provisional application No. 60/260,505, filed on Jul. 9, 2001.

(51) Int. Cl.
*C07D 413/06* (2006.01)
*C07D 401/06* (2006.01)
*C07D 406/06* (2006.01)

(52) U.S. Cl. ............... 544/141; 546/208; 548/517
(58) Field of Classification Search ............... 544/141; 546/208; 548/517
See application file for complete search history.

(56) References Cited

U.S. PATENT DOCUMENTS

| 4,681,893 A | 7/1987 | Roth | 514/422 |
|---|---|---|---|
| 5,003,080 A | 3/1991 | Butler et al. | 457/517 |
| 5,097,045 A | 3/1992 | Butler et al. | 549/373 |
| 5,103,024 A | 4/1992 | Millar et al. | 549/373 |
| 5,124,482 A | 6/1992 | Butler et al. | 546/169 |
| 5,149,837 A | 9/1992 | Butler et al. | 549/333 |
| 5,155,251 A | 10/1992 | Butler et al. | 558/442 |
| 5,216,174 A | 6/1993 | Butler et al. | 548/517 |
| 5,245,047 A | 9/1993 | Butler et al. | 548/517 |
| 5,248,793 A | 9/1993 | Millar et al. | 549/375 |
| 5,273,995 A | 12/1993 | Roth | 514/422 |
| 5,280,126 A | 1/1994 | Butler et al. | 548/517 |
| 5,298,627 A | 3/1994 | Butler et al. | 548/517 |
| 5,342,952 A | 8/1994 | Butler et al. | 546/245 |
| 5,397,792 A | 3/1995 | Butler et al. | 514/326 |
| 5,446,054 A | 8/1995 | Butler et al. | 514/326 |
| 5,470,981 A | 11/1995 | Butler et al. | 546/207 |
| 5,489,690 A | 2/1996 | Butler et al. | 546/245 |
| 5,489,691 A | 2/1996 | Butler et al. | 548/517 |
| 5,510,488 A | 4/1996 | Butler et al. | 546/207 |
| 5,969,156 A | 10/1999 | Briggs et al. | 548/537 |
| 5,998,633 A | 12/1999 | Jacks et al. | 549/313 |
| 6,087,511 A | 7/2000 | Lin et al. | 548/537 |
| 6,121,461 A | 9/2000 | McKenzie | 548/530 |

OTHER PUBLICATIONS

*Tetrahedron Letters*, vol. 32, No. 52, 1991, pp. 7699-7702, Shao et al.
*Tetrahedron*, vol. 49, No. 10, 1993, pp. 1997-2010, Shao et al.
*Tetrahedron Letters*, vol. 32, No. 34, 1991, pp. 4227-4230, Taber et al.
*Tetrahedron Letters*, vol. 29, No. 11, 1988, pp. 1255-1258, Roth et al.
*Journal of Organic Chemistry*, vol. 57, 1992, pp. 6689-6691, King et al.
*European Journal of Organic Chemistry*, 1999, pp. 3421-3427, Blandin et al.
*Acc. Chem. Res.*, vol. 23, 1990, pp. 345-350, Noyori et al.

*Primary Examiner*—Kamal A. Saeed
(74) *Attorney, Agent, or Firm*—Francis J. Tinney; Charles W. Ashbrook

(57) ABSTRACT

An improved process for the preparation of 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide by a novel synthesis is described where methyl cyanoacetate is converted in eight operations or fewer to the desired product, as well as other valuable intermediates used in the process.

2 Claims, No Drawings

PROCESS FOR THE SYNTHESIS OF 5-(4-FLUOROPHENYL)-1-[2-((2R,4R)-4-HYDROXY-6-OXO-TETRAHYDRO-PYRAN-2-YL)-ETHYL]-2-ISOPROPYL-4-PHENYL-1H-PYRROLE-3-CARBOXYLIC ACID PHENYLAMIDE

This application is a divisional application of U.S. Ser. No. 10/348,727, filed Jan. 21, 2003, now U.S. Pat. No. 6,933,393, which is a divisional of U.S. Ser. No. 10/198,682, filed Jul. 18, 2002, now U.S. Pat. No. 6,545,153, which is a divisional application of U.S. Ser. No. 10/015,558, filed Dec. 17, 2001, now U.S. Pat. No. 6,476,235 B2, which claims benefit of Provisional Application U.S. Ser. No. 60/260,505, flied Jul. 9, 2001.

FIELD OF THE INVENTION

An improved synthesis for the preparation of 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide is described where methyl cyanoacetate is converted in eight operations or fewer to the desired product, as well as other valuable intermediates used in the process.

BACKGROUND OF THE INVENTION 5-(4-Fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide is a valuable intermediate in the synthesis of Lipitor® (atorvastatin calcium) known by the chemical name [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1) trihydrate. The aforementioned compound is useful as an inhibitor of the enzyme 3-hydroxy-3-methylglutaryl-coenzyme A reductase (HMG-COA reductase) and is thus useful as a hypolipidemic and/or hypocholesterolemic agent.

U.S. Pat. No. 4,681,893, which is herein incorporated by reference, discloses certain trans-6-[2-(3- or 4-carboxamido-substituted-pyrrol-1-yl)alkyl]-4-hydroxy-pyran-2-ones including trans (±)-5-(4-fluorophenyl)-2-(1-methylethyl)-N,4-diphenyl-1-](2-tetrahydro-4-hydroxy-6-oxo-2H-pyran-2-yl)ethyl]-1H-pyrrole-3-carboxamide.

U.S. Pat. No. 5,273,995, which is herein incorporated by reference, discloses the enantiomer having the (R,R) form of the ring-opened acid of trans-5-(4-fluorophenyl)-2-(1-methylethyl)-N, 4-diphenyl-1-[(2-tetrahydro-4-hydroxy-6-oxo-2H-pyran-2-yl)ethyl]-1H-pyrrole-3-carboxamide, i.e., [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid.

U.S. Pat. Nos. 5,003,080; 5,097,045; 5,103,024; 5,124,482; 5,149,837; 5,155,251; 5,216,174; 5,245,047; 5,248,793; 5,280,126; 5,397,792; 5,342,952; 5,298,627; 5,446,054; 5,470,981; 5,489,690; 5,489,691; 5,510,488; 5,998,633; and 6,087,511, which are herein incorporated by reference, disclose various processes and key intermediates for preparing atorvastatin.

Crystalline forms of atorvastatin calcium are disclosed in U.S. Pat. Nos. 5,969,156 and 6,121,461 which are herein incorporated by reference.

A synthetic procedure for the preparation of 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide is disclosed in U.S. Pat. No. 5,273,995.

The asymmetric reduction of β-ketoesters, as well as β-diketones, is a well-established transformation in organic synthesis. However, the complexity of these reactions increases in the case of 1,3,5-tricarbonyl systems and poor yields and poor stereoselectivities often result. In fact, investigations by Saburi (*Tetrahedron*, 1997, 1993;49) and Carpentier (*Eur. J. Org. Chem.* 1999;3421) have independently demonstrated low to moderate diastereo- and/or enantio-selectivities for diketoester asymmetric hydrogenations. Furthermore, the fact that the processes in the prior art require high pressure hydrogenation and extended reaction times makes these procedures impractical and not amenable to large-scale manufacturing processes.

However, we have surprisingly and unexpectedly found that the diol esters of the present invention, (R)-7-[2-(4-fluorophenyl)-5-isopropyl-3-phenyl-4-phenylcarbamoyl-pyrrol-1-yl]-3,5-dihydroxy-heptanoic acid esters, can be obtained directly from the corresponding 1,3,5-tricarbonyl precursors in a highly stereoselective manner via a mild and efficient ruthenium-catalyzed asymmetric hydrogenation reaction utilizing chiral non-racemic diphosphine ligands in the presence of secondary activating agents such as protic acids.

The object of the present invention is a short and efficient process for the preparation of 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide. The present process avoids the use of a costly chiral raw material ((R)-4-cyano-3-hydroxy-butyric acid ethyl ester), and a low temperature diastereoselective borane reduction. Furthermore, a key Paal-Knorr condensation step, common to the present and prior art processes, has been improved through a significant decrease in reaction time.

Thus, the present process has significant advantages over the prior art processes and is amenable to large-scale synthesis.

SUMMARY OF THE INVENTION

Accordingly, the first aspect of the present invention is an improved process for the preparation of a compound of Formula (13)

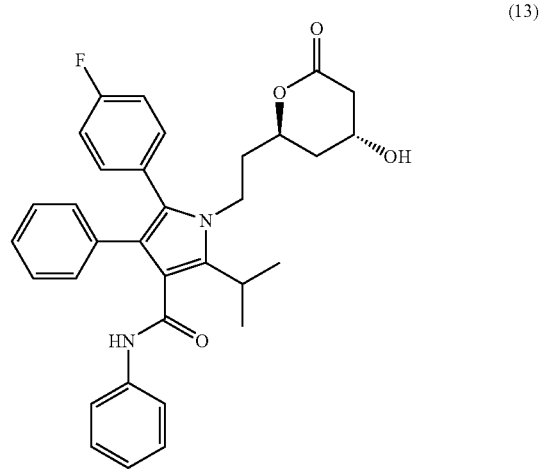

(13)

which comprises:

Step (a) reacting a compound of Formula (1)

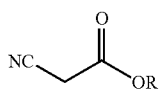
(1)

wherein R is alkyl, aryl, arylalkyl, or heteroaryl in a solvent with a compound of Formula (2)

$R^1$—H (2)

wherein $R^1$ is —XR wherein
X is O,
S, or
Se, or $R^1$ is

wherein $R^2$ or $R^3$ is independently
alkyl,
cycloalkyl,
arylalkyl, or
aryl, or
$R^2$ and $R^3$ together are
—(CH$_2$)$_4$—,
—(CH$_2$)$_5$—,
—(CH(R$^4$)—CH$_2$)$_3$—,
—(CH(R$^4$)—CH$_2$)$_4$—,
—(CH(R$^4$)—(CH$_2$)$_2$—CH(R$^4$))—,
—(CH(R$^4$)—(CH$_2$)$_3$—CH(R$^4$))—,
—CH$_2$—CH$_2$-A-CH$_2$—CH$_2$—,
—CH(R$^4$)—CH$_2$-A-CH$_2$CH$_2$—,
—CH(R$^4$)—CH$_2$-A-CH$_2$—CH(R$^4$)— wherein $R^4$ is alkyl of from one to four carbon atoms, A is O, S, or N and R is as defined above to afford a compound of Formula (3)

(3)

wherein $R^1$ is as defined above;

Step (b) reacting a compound of Formula (3) with hydrogen in the presence of a catalyst and a strong acid in a solvent to afford a compound of Formula (4)

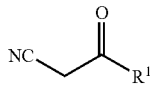
(4)

wherein Y is Cl, Br, TsO, MsO, or HSO$_4$, and $R^1$ is as defined above;

Step (c) reacting a compound of Formula (4) with a base in a solvent followed by the addition of a compound of Formula (5)

R—CO$_2$H (5)

wherein R is as defined above in a solvent to afford a compound of Formula (6)

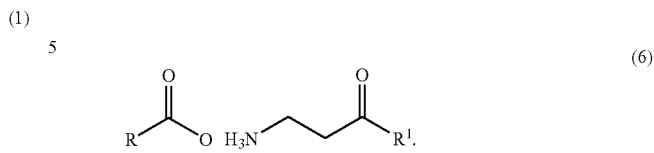
(6)

wherein R and $R^1$ are as defined above;

Step (d) reacting a compound of Formula (6) with Compound (7)

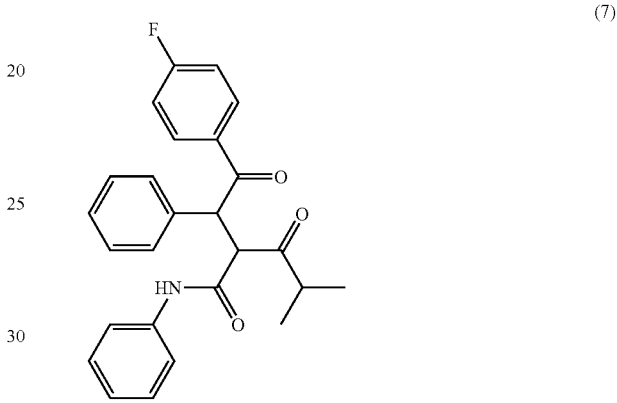
(7)

in a solvent with removal of water to afford a compound of Formula (8)

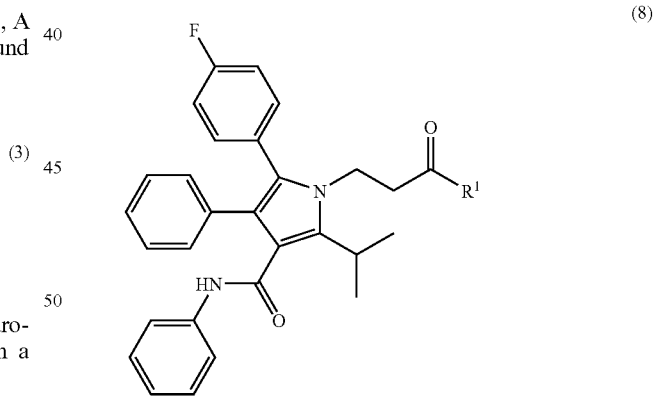
(8)

wherein $R^1$ is as defined above;

Step (e) reacting a compound of Formula (8) with a compound of Formula (9)

(9)

wherein M is sodium, lithium, potassium, zinc, magnesium, copper, calcium, or aluminum and $R^1$ is as defined above, in a solvent in the presence of a strong base to afford a compound of Formula (10)

(10)

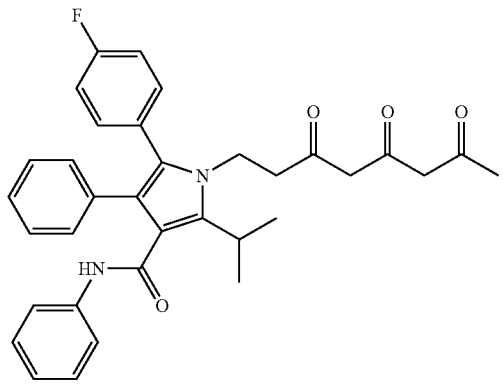

wherein $R^1$ is as defined above;

Step (f) reacting a compound of Formula (10) with hydrogen in the presence of a catalyst in a solvent in the presence of an acid to afford a compound of Formula (11)

(11)

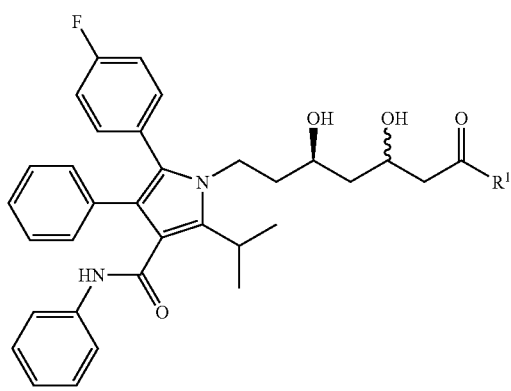

wherein $R^1$ is as defined above or a compound of Formula (11a)

(11a)

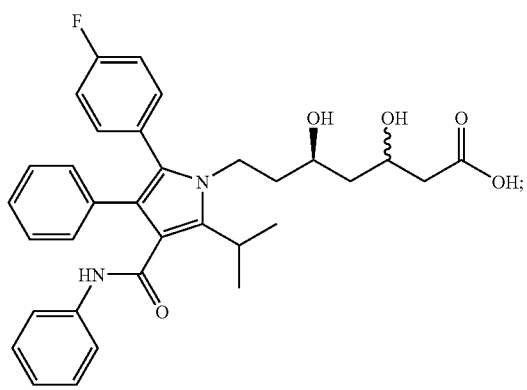

Step (g) reacting a compound of Formula (11b)

(11b)

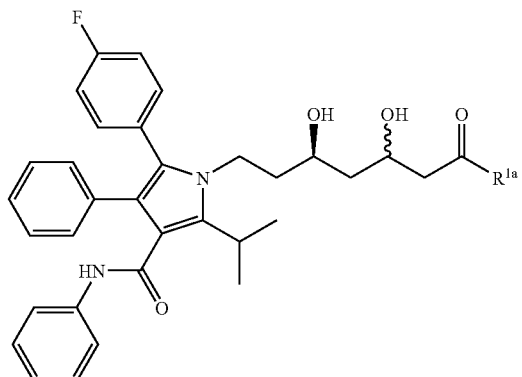

wherein $R^{1a}$ is OH, —XR wherein
X is O,
S, or
Se, or $R^{1a}$ is

wherein $R^2$ or $R^3$ is independently
alkyl,
cycloalkyl,
arylalkyl, or
aryl, or
$R^2$ and $R^3$ together are
—$(CH_2)_4$—,
—$(CH_2)_5$—,
—$CH(R^4)$—$CH_2)_3$—,
—$CH(R^4)$—$CH_2)_4$—,
—$CH(R^4)$—$(CH_2)_2$—$CH(R^4)$)—,
—$CH(R^4)$—$(CH_2)_3$—$CH(R^4)$)—,
—$CH_2$—$CH_2$-A-$CH_2$—$CH_2$—,
—$CH(R^4)$—$CH_2$-A-$CH_2CH_2$—,
—$CH(R^4)$—$CH_2$-A-$CH_2$—$CH(R^4)$—
wherein $R^4$ is alkyl of from one to four carbon atoms, A is O, S, or N, and R is as defined above in a solvent in the presence of an acid, followed by reaction with a base, an acylating agent, and an acylation catalyst in a solvent to afford a compound of Formula (12)

(12)

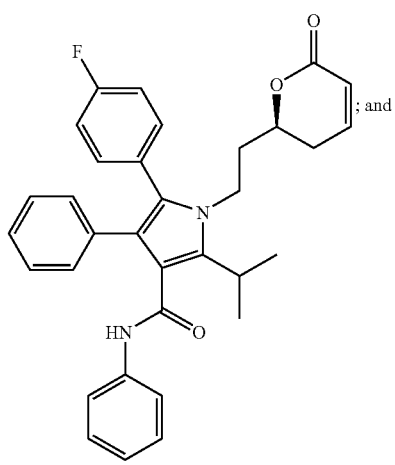

Step (h) reacting a compound of Formula (12) with HO-M in an alcohol of Formula (17) or (17b)

HOCH$_2$-Aryl (17) or HO-Allyl (17b)

wherein M is sodium, lithium, potassium, zinc, magnesium, copper, calcium, or aluminum; or with a compound of Formula (16) or (16b)

M OCH$_2$-Aryl (16) or M O-Allyl          (16b)

wherein M is as defined above in an alcohol of Formula (17) or (17b) wherein aryl or allyl in a compound of Formula (16) or (16b) and (17) or (17b) is the same, in a solvent followed by the addition of hydrogen in the presence of a catalyst and an acid to afford the compound of Formula (13).

A second aspect of the present invention is an improved process for the preparation of a compound of Formula (8).

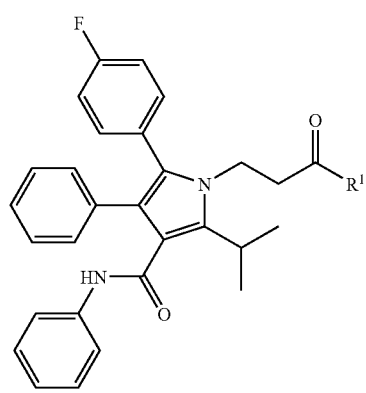

(8)

wherein R$^1$ is as defined above which comprises:
reacting a compound of Formula (4)

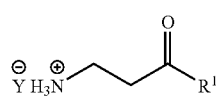

(4)

wherein Y is Cl, Br, TsO, MsO, or HSO$_4$, and R$^1$ is as defined above with a compound of Formula (20)

R—CO$_2$ M          (20)

wherein R and M are as defined above with Compound (7)

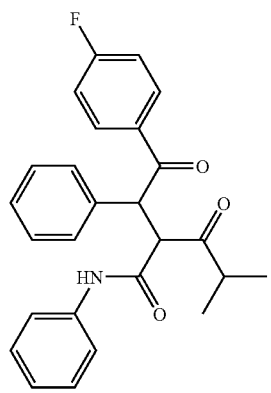

(7)

in a solvent with removal of water to afford a compound of Formula (8).

A third aspect of the present invention is an improved process for the preparation of compound (13)

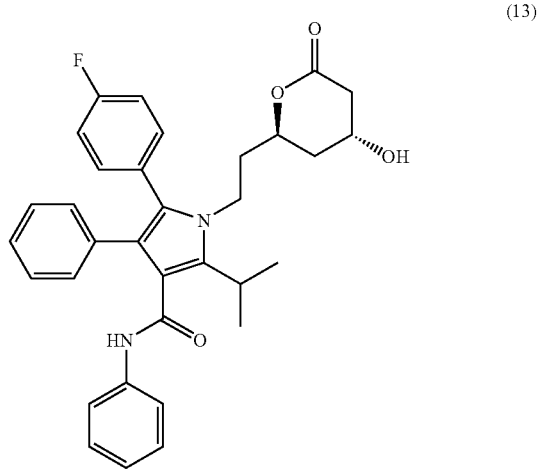

(13)

which comprises:

Step (a) reacting a compound of Formula (11) with an acetal of Formula (15)

(15)

wherein R$^5$ and R$^5$a are independently the same or different and are, methyl, ethyl, or —(CH$_2$)$_n$— wherein n is an integer of 2 to 4, and R is as defined above in a solvent in the presence of an acid followed by the addition of an aldehyde corresponding to the previous acetal in the presence of a base to afford a compound of Formula (14)

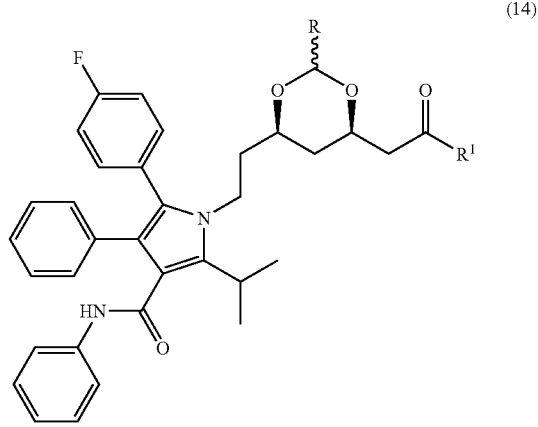

(14)

wherein R$^1$ and R are as defined above;

Step (b) reacting a compound of Formula (14) in a nucleophilic solvent in the presence of an acid or optionally reaction with hydrogen in the presence of a catalyst and an acid in a solvent to afford the compound of Formula (13); and Step (c) alternatively, reacting a compound of Formula (11) or (11a) in a non-nucleophilic solvent in the presence of an acid to afford a compound of Formula (13).

A fourth aspect of the present invention is a process for the preparation of a compound of Formula (11b)

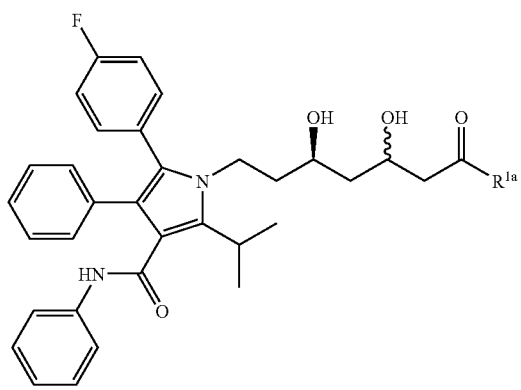

(11b)

wherein $R^{1a}$ is OH, —XR wherein

X is O,

S, or

Se, or $R^{1a}$ is

wherein $R^2$ or $R^3$ is independently alkyl, cycloalkyl, arylalkyl, or aryl, or $R^2$ and $R^3$ together are

—(CH$_2$)$_4$—,

—(CH$_2$)$_5$—,

—(CH(R$^4$)—CH$_2$)$_3$—,

—(CH(R$^4$)—CH$_2$)$_4$—,

—(CH(R$^4$)—(CH$_2$)$_2$—CH(R$^4$))—,

—(CH(R$^4$)—(CH$_2$)$_3$—CH(R$^4$))—,

—CH$_2$—CH$_2$-A-CH$_2$—CH$_2$—,

—CH(R$^4$)—CH$_2$-A-CH$_2$CH$_2$—,

—CH(R$^4$)—CH$_2$-A-CH$_2$—CH(R$^4$)— wherein $R^4$ is alkyl of from one to four carbon atoms, A is O, S, or N, and R is alkyl, aryl, arylalkyl, or heteroaryl which comprises:

Step (a) reacting a compound of Formula (10)

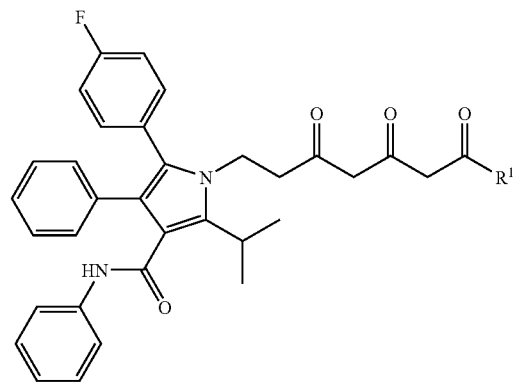

(10)

wherein $R^1$ is as defined above with one mole of hydrogen in the presence of a catalyst in a solvent in the presence of an acid to afford compounds of Formula (18) and/or Formula (18a)

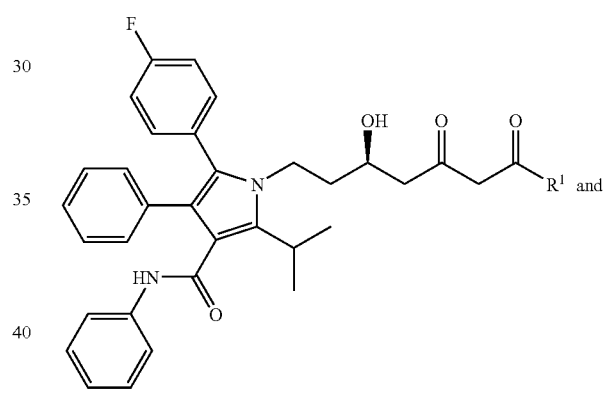

(18)

and

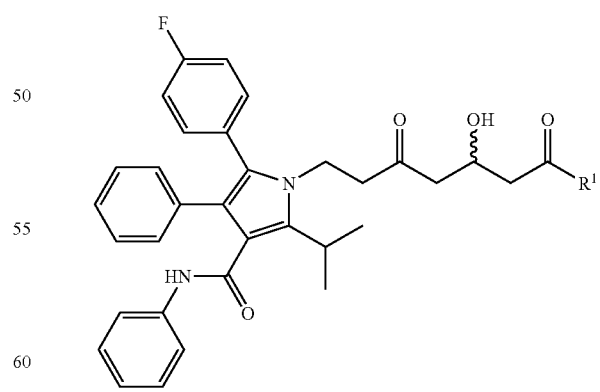

(18a)

wherein $R^1$ is as defined above; and

Step (b) reacting either a compound of Formula (18) or (18a) with hydrogen in the presence of a catalyst in a solvent in the presence of an acid to afford a compound of Formula (11b).

A fifth aspect of the present invention is a compound of Formula (6)

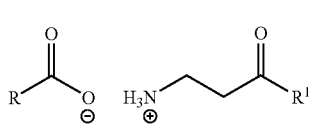
(6)

wherein R is alkyl, aryl, arylalkyl, or heteroaryl, and $R^1$ is XR wherein
X is O,
S, or
Se, or $R^1$ is

wherein $R^2$ or $R^3$ is independently
alkyl,
cycloalkyl,
arylalkyl, or
aryl or
$R^2$ and $R^3$ together are
—(CH$_2$)$_4$—,
—(CH$_2$)$_5$—,
—(CH(R$^4$)—CH$_2$)$_3$—,
—(CH(R$^4$)—CH$_2$)$_4$—,
—(CH(R$^4$)—(CH$_2$)$_2$—CH(R$^4$))—,
—(CH(R$^4$)—(CH$_2$)$_3$—CH(R$^4$))—,
—CH$_2$—CH$_2$-A-CH$_2$—CH$_2$—,
—CH(R$^4$)—CH$_2$-A-CH$_2$CH$_2$—,
—CH(R$^4$)—CH$_2$-A-CH$_2$—CH(R$^4$)— wherein $R^4$ is alkyl of from one to four carbon atoms, A is O, S, or N and R is as defined above.

Particularly preferred, is a compound of Formula (6) wherein R is PhCH$_2$— or (CH$_3$)$_3$—C—, and $R^1$ is

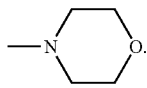

More particularly preferred, is a compound of Formula (6) wherein R is PhCH$_2$— and $R^1$ is

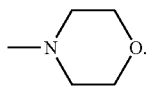

A sixth aspect of the present invention is a compound of Formula (8)

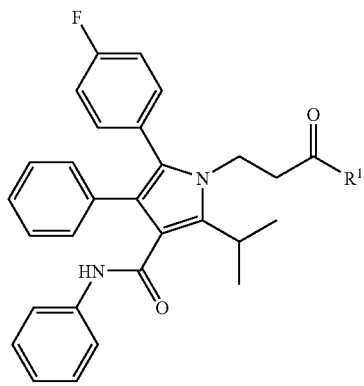
(8)

wherein $R^1$ is as defined above.

Particularly preferred is a compound of Formula (8) wherein $R^1$ is

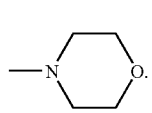

A seventh aspect of the present invention is a compound of Formula (10) or a pharmaceutically acceptable salt thereof

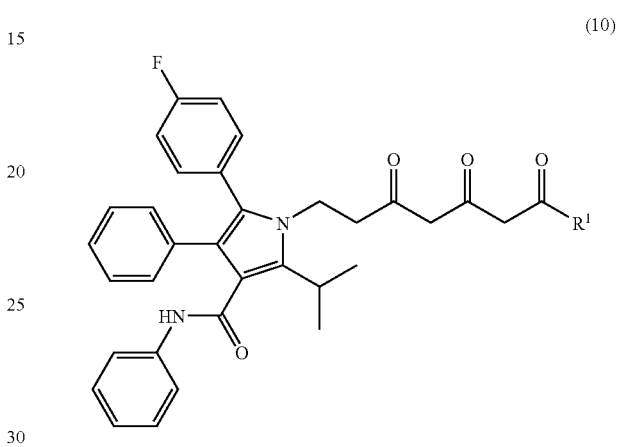
(10)

wherein $R^1$ is as defined above.

Particularly preferred is a compound of Formula (10) wherein $R^1$ is —O-tertiary butyl, —O-isopropyl, —O-ethyl, —O-methyl,

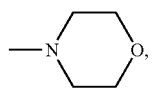

or —NMe$_2$.

An eighth aspect of the present invention is the compound of Formula (12)

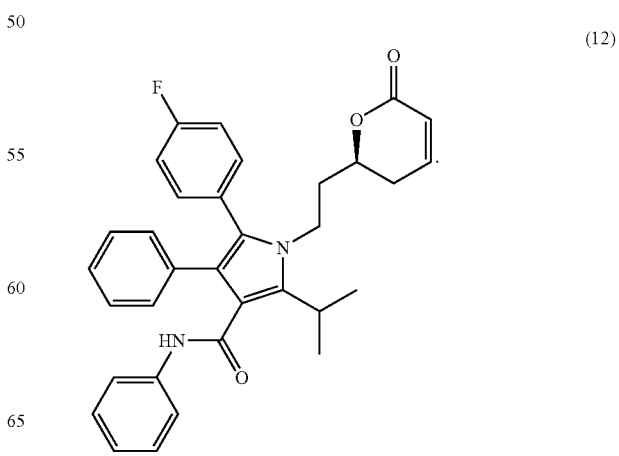
(12)

A ninth aspect of the present invention is a compound of Formula (18) or a pharmaceutically acceptable salt thereof

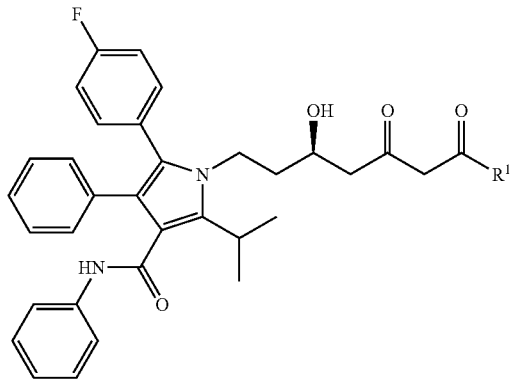

wherein $R^1$ is as defined above.

Particularly preferred is a compound of Formula (18) wherein $R^1$ is —O-tertiary butyl, —O-isopropyl, —O-ethyl, —O-methyl,

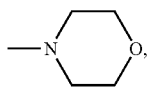

or —NMe$_2$.

A tenth aspect of the present invention is a compound of Formula (18a) or a pharmaceutically acceptable salt thereof (18a)

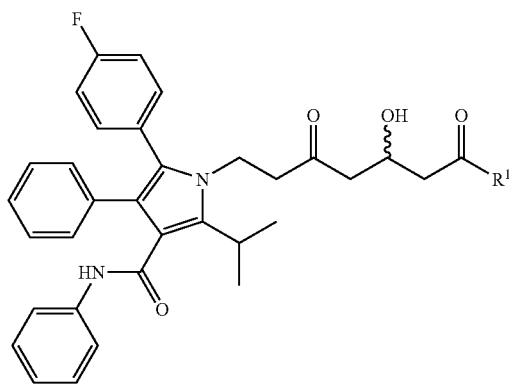

wherein $R^1$ is as defined above.

Particularly preferred is a compound of Formula (18a) wherein $R^1$ is —O-tertiary butyl, —O-isopropyl, —O-ethyl, —O-methyl,

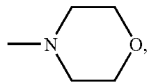

or —NMe$_2$.

DETAILED DESCRIPTION OF THE INVENTION

The term "alkyl" means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

"Alkoxy" and "thioalkoxy" are O-alkyl or S-alkyl of from 1 to 6 carbon atoms as defined above for "alkyl".

The term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

The term "aryl" means an aromatic radical which is a phenyl group, a phenylalkyl group, a phenyl group substituted by 1 to 4 substituents selected from alkyl as defined above, alkoxy as defined above, thioalkoxy as defined above, halogen, trifluoromethyl, dialkylamino as defined above for alkyl, nitro, cyano,

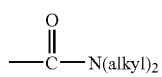

as defined above for alkyl, —(CH$_2$)$_{n^2}$-N(alkyl)$_2$ wherein $n^2$ is an integer of 1 to 5 and alkyl is defined above and

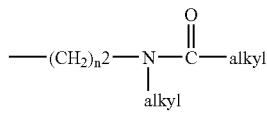

as defined above for alkyl and $n^2$.

The term "allyl" means a hydrocarbon radical of 3 to 8 carbon atoms, containing a double bond between carbons 2 and 3, unsubstituted or substituted by 1 to 3 substituents on the carbons containing the double bond selected from alkyl or aryl as defined above, and includes, for example, propenyl, 2-butenyl, cinnamyl, and the like.

The term "arylalkyl" means an aromatic radical attached to an alkyl radical wherein aryl and alkyl are as defined above for example, benzyl, phenylethyl, 3-phenylpropyl, (4-chlorophenyl)methyl, and the like.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium, and the like.

The term "heteroaryl" means a 5- and 6-membered heteroaromatic radical which may optionally be fused to a benzene ring containing 1 to 3 heteroatoms selected from N, O, and S and includes, for example, a heteroaromatic radical which is 2- or 3-thienyl, 2- or 3-furanyl, 2- or 3-pyrrolyl, 2-, 3-, or 4-pyridinyl, 2-pyrazinyl, 2-, 4-, or 5-pyrimidinyl, 3- or 4-pyridazinyl, 1H-indol-6-yl, 1H-indol-5-yl, 1H-benzimida zol-6-yl, 1H-benzimidazol-5-yl, 2-, 4-, or 5-thiazolyl, 3-, 4-, or 5-isothiazolyl, 2-, 4-, or 5-imidazolyl, 3-, 4-, or 5-pyrazolyl, or 2- or 5-thiadiazolyl and the like optionally substituted by a substituent selected from alkyl as defined above, alkoxy as defined above, thioalkoxy as defined above, halogen, trifluoromethyl, dialkylamino as defined above for alkyl, nitro, cyano,

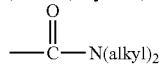

as defined above for alkyl, —(CH2)$_{n}$2-N(alkyl)$_2$ wherein n$^2$ is an integer of 1 to 5, and alkyl is as defined above, and

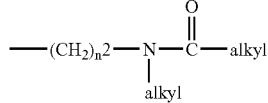

as defined above for alkyl and n$^2$.

Pharmaceutically acceptable acid addition salts of the compounds of the present invention include salts derived from inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M. et al., "Pharmaceutical Salts," *J. of Pharma. Sci.*, 1977;66:1).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M. et al., "Pharmaceutical Salts," *J. of Pharma Sci.*, 1977;66: 1).

The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Additionally, the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The following list contains abbreviations and acronyms used within the schemes and text:
H$_2$SO$_4$ Sulfuric acid
NaOMe Sodium methoxide
MeOH Methanol
MtBE Methyl tert-butyl ether
GC Gas chromatography
Pt/C Platinum on carbon
Pd/C Palladium on carbon
H$_2$ Hydrogen
HCl Hydrochloric acid
Hg Mercury
psi Pounds per square inch
iPrOH (IPA) Isopropyl alcohol
HPLC High pressure liquid chromatography
NaOH Sodium hydroxide
CH$_2$Cl$_2$ Dichloromethane (methylene chloride)
DMSO-d$_6$ Deuterated dimethylsulfoxide
THF Tetrahydrofuran
Na$_2$SO$_4$ Sodium sulfate
nBuLi n-Butyllithium
NaCl Sodium chloride
KOtBu Potassium tert-butoxide
NaHCO$_3$ Sodium bicarbonate
BnOH Benzyl alcohol
Pd(OH)$_2$/C Palladium hydroxide on carbon
H$_2$O Water
PivOH Pivalic acid
PhCHO Benzaldehyde
PhCH$_3$ Toluene
CDCl$_3$ Deuterated chloroform
BnONa Sodium benzylate
NH$_4$OH Ammonium hydroxide
PhCH(OMe)$_2$ Benzaldehyde dimethyl acetal
MsOH Methanesulfonic acid
pTsOH para Toluenesulfonic acid
CSA Camphorsulfonic acid
Ph Phenyl
NaH Sodium hydride
KH Potassium hydride
EtOAc Ethyl acetate
tBuOH(HOtBu) tert-Butanol
PhCH$_2$CO$_2$H Phenylacetic acid
NaNH$_2$ Sodium amide
KHMDS Potassium hexamethyldisilazide
LAH Lithium aluminum hydride
Pd/Al$_2$O$_3$ Palladium on alumina
APCI Atmospheric pressure chemical ionization
ESI Electrospray ionization
DCI Direct chemical ionization
$^1$H NMR Proton nuclear magnetic resonance spectroscopy
$^{13}$C NMR $^{13}$Carbon nuclear magnetic resonance spectroscopy
BINAP (R)-(+)-2,2'-Bis(diphenylphosphino)-1,1'-binaphthyl
pTol-BINAP (R)-(+)-Bis(di-p-tolyl-phosphino)-1,1'-binaphthyl
C1-MeO-BIPHEP [(R)-(+)-5,5'-Dichloro-6,6'-dimethoxy [1,1'-biphenyl]-2,2'-diyl]-bis-diphenylphosphine
C2-TunaPhos [(12aR)-6,7-dihydrodibenzo[e,g] [1,4]dioxocin-1,12-diyl]-bis-diphenylphosphine
C4-TunaPhos [(14aR)-6,7,8,9-tetrahydrodibenzo[b,d][1,6] dioxecin-1,14-diyl]-bis-diphenylphosphine MeO-BIPHEP [(1S)-(−)-6,6'-Dimethoxy [1,1'-biphenyl]-2, 2'-diyl]-bis-diphenylphosphine
p-cymene 4-isopropyltoluene
ee Enantiomeric excess
HRMS High resolution mass spectrometry
m/z Mass to charge ratio
$t_R$ Retention time The process of the present invention in its first aspect is a new, improved, economical, and commercially feasible method for the preparation of the compound of Formula (13)

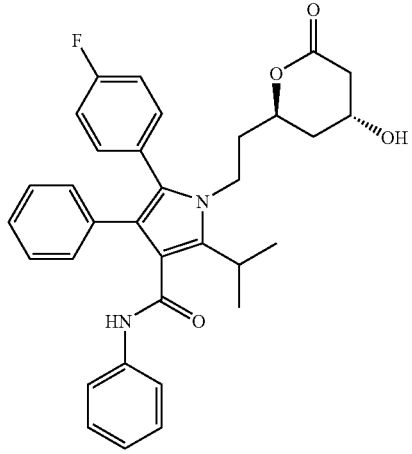

(13)

The process of the present invention in its first aspect is outlined in Scheme 1. Thus, a compound of Formula (1) wherein R is alkyl, aryl, arylalkyl, or heteroaryl is reacted with a compound of Formula (2) wherein $R^1$ is —XR- wherein
X is O,
S,
Se or $R^1$ is

wherein $R^2$ or $R^3$ is independently
alkyl,
cycloalkyl,
arylalkyl, or
aryl, or
$R^2$ and $R^3$ together are
—$(CH_2)_4$—,
—$(CH_2)_5$—,
—$(CH(R^4)$—$CH_2)_3$—,
—$(CH(R^4)$—$CH_2)_4$—,
—$(CH(R^4)$—$(CH_2)_2$—$CH(R^4))$—,
—$(CH(R^4)$—$(CH_2)_3$—$CH(R^4))$—,
—$CH_2$—$CH_2$-A-$CH_2$—$CH_2$—,
—$CH(R^4)$—$CH_2$-A-$CH_2CH_2$—,
—$CH(R^4)$—$CH_2$-A-$CH_2$—$CH(R^4)$— wherein $R^4$ is alkyl of from one to four carbon atoms, A is O, S, or N and R is as defined above in a solvent such as, for example, methyl tertiary butyl ether, and the like, to afford a compound of Formula (3) whereas $R^1$ is as defined above. Preferably, the reaction is carried out with a compound of Formula (2) wherein $R^1$—H is morpholine in methyl tertiary butyl ether.

A compound of Formula (3) is reacted with hydrogen in the presence of a catalyst such as, for example, Pt/C, Pd/C in the presence of an acid such as, for example, a strong acid, for example, hydrochloric acid, hydrobromic acid, p-tolu- enesulfonic acid, methanesulfonic acid, sulfuric acid, and the like (optionally the reduction is carried out with Sponge Ni/NH$_4$OH, metal hydrides, and the like, to afford the free base of a compound of Formula (4)) in a solvent such as, for example, methanol, ethanol, and the like to afford a compound of Formula (4) wherein Y is Cl, Br, TsO, MsO, or HSO$_4$ and $R^1$ is as defined above.

Preferably, the reaction is carried out in the presence of Pt/C, hydrochloric acid and hydrogen in methanol.

A compound of Formula (4) is reacted with a base such as, for example, sodium methoxide and the like in a solvent such as, for example, tetrahydrofuran, toluene, methyl tertiary butyl ether, and the like, and in an alcohol such as, for example, isopropanol, ethanol, methanol, and the like, to afford the free base followed by reaction with a compound of Formula (5) wherein R is as defined above in a solvent such as, for example, isopropanol, tetrahydrofuran, and the like to afford a compound of Formula (6) wherein R is as defined above. Optionally, the free base of a compound of Formula (4) may be reacted with a compound of Formula (5) to afford a compound of Formula (6). Preferably, the reaction is carried out with sodium methoxide in methyl tertiary butyl ether and methanol to afford the free base followed by reaction with phenylacetic in tetrahydrofuran.

A compound of Formula (6) is reacted with the compound of Formula (7) in a solvent such as, for example, a protic, an aprotic, a polar or a non-polar solvent, for example, tetrahydrofuran and the like with removal of water with the aid of a chemical drying agent such as, for example, molecular sieves and the like or with the aid of a Dean-Stark water trap or using azeotropic distillation with a suitable solvent such as, for example toluene and the like to afford a compound of Formula (8) wherein $R^1$ is as defined above. Preferably, the reaction is carried out with activated 3A molecular sieves in tetrahydrofuran.

A compound of Formula (8) is reacted with a compound of Formula (9) wherein M is sodium, lithium, potassium, zinc, magnesium, copper, calcium, or aluminum and $R^1$ is as defined above in a solvent such as, for example, a nonreactive aprotic solvent, for example, tetrahydrofuran, toluene, and the like in the presence of a strong base such as, for example, n-butyllithium, lithium or potassium hexamethyldisilazide, lithium diisopropylamide, and the like to afford a compound of Formula (10) wherein $R^1$ is as defined above. Preferably, the reaction is carried out with a compound of Formula (9) wherein M is sodium, the base is n-butyllithium and the solvent is tetrahydrofuran.

The carbonyls of a compound of Formula (10) in Scheme 1 are shown in the keto form. However, a compound of Formula (10) can undergo "keto-enol" tautomerism and thus can exist in several tautomeric forms which are encompassed within the present invention.

A compound of Formula (10) is treated with hydrogen in the presence of a catalyst such as, for example, a chiral non-racemic ruthenium (II)-diphosphine complex. For example, a ruthenium catalyst precursor such as [dichloro-(1,5-cyclooctadiene)]ruthenium (II) oligomer and chiral diphosphine ligand such as [(R)-(+)-2,2'-bis(diphenyl-phosphino)-1,1'-binaphthyl]. However, any chiral non-racemic ruthenium (II)/diphosphine combination may be employed in this reduction reaction. For example, ruthenium (II) catalyst precursors include [dibromo-(1,5-cyclooctadiene)] ruthenium (II) dimer, [bis-(2-methallyl)cycloocta-1,5-diene] ruthenium (II) complex and [dichloro(p-cymene)] ruthenium (II) dimer, and the like. Examples of effective chiral diphosphine ligands include 2,2'-bis(di-p-tolyl-phosphino)-1,1'-binaphthyl, 2-diphenyl-phosphinomethyl-4-diphenylphosphino-1-tert-butoxy-carbonylpyrrolidine, tricyclo [8.2.2.2$^{4,7}$]hexadeca-4,6, 10,12,13,15-hexaene-5,11-diylbis(diphenylphosphine) derivatives, 4,4'-bidibenzofuran-3,3'-diylbis(diphenylphosphine), 6,6'-dimethoxy[1,1'-biphenyl]-2,2'-diyl]bis-diphenylphosphine, [5,5'-dichloro-6,6'-dimethoxy[1,1'-biphenyl]-2,2'-diyl]-bis-diphenylphosphine, and 1,2-bis(2,5-dimethylphospholano) derivatives and the like in a solvent such as, for example, methanol, ethanol, isopropanol, and the like, optionally in the presence of a co-solvent, for example, dichloromethane, tetrahydrofuran, toluene and the like in the presence of an acid such as, for example, hydrochloric acid, hydrobromic acid, Dowex® ion exchange resin, and the like to afford a compound of Formula (11) or a compound of Formula (11a) wherein $R^1$ is as defined above. Preferably, the reaction is carried out with dichloro(p-cymene) ruthenium (II) dimer and [(R)-(+)-5,5'-dichloro-6,6'-dimethoxy[1,1'-biphenyl]-2,2'-diyl]-bis-diphenylphosphine in methanol in the presence of hydrobromic acid.

A compound of Formula (11b) wherein $R^1a$ is wherein $R^{1a}$ is OH, —XR wherein
X is O,
S, or
Se, or $R^{1a}$ is

wherein $R^2$ or $R^3$ is independently
alkyl,
cycloalkyl,
arylalkyl, or
aryl, or
$R^2$ and $R^3$ together are
—$(CH_2)_4$—,
—$(CH_2)_5$—,
—$(CH(R^4)$—$CH_2)_3$—,
—$(CH(R^4)$—$CH_2)_4$—,
—$(CH(R^4)$—$(CH_2)_2$—$CH(R^4))$—,
—$(CH(R^4)$—$(CH_2)_3$—$CH(R^4))$—,
—$CH_2$—$CH_2$-A-$CH_2$—$CH_2$—,
—$CH(R^4)$—$CH_2$-A-$CH_2CH_2$—,
—$CH(R^4)$—$CH_2$-A-$CH_2$—$CH(R^4)$—
wherein $R^4$ is alkyl of from one to four carbon atoms, A is O, S, or N, and R is alkyl, aryl, arylalkyl, or heteroaryl is reacted with an acid such as, for example, p-toluenesulfonic acid, camphor-sulfonic acid, sulfuric acid, hydrogen chloride, and the like in a non-nucleophilic solvent such as, for example, toluene, acetonitrile, dichloromethane, methyl tertiary butyl ether, and the like, followed by reaction with a base, such as, for example, triethylamine, pyridine, diisopropylethylamine, and the like, and with an acylating agent, such as, for example, acetic anhydride, benzoyl chloride, benzyl chloroformate, and the like, in the presence of 4-dimethylaminopyridine to afford the compound of Formula (12). Preferably, the reaction is carried out in toluene in the presence of p-toluenesulfonic acid, followed by treatment with triethylamine, acetic anhydride, and 4-dimethylaminopyridine in toluene.

A compound of Formula (12) is reacted with HO-M in an alcohol of Formula (17) or (17b) wherein M is sodium, lithium, potassium, zinc, magnesium, copper, calcium, or aluminum, or with a compound of Formula (16) or (16b) wherein M is as defined above in an alcohol of Formula (17) or (17b) wherein aryl or allyl in a compound of Formula (16) or (16b) and (17) or (17b) is the same, in an optional cosolvent, such as, for example, a normucleophilic solvent, for example, acetone, tetrahydrofuran, 1,2-dimethoxyethane, and the like, followed by the addition of hydrogen in the presence of a catalyst, such as, for example, $Pd(OH)_2/C$, $Pd/C$, $Pd/Al_2O_3$, and the like, in the presence of an acid, such as, for example, hydrochloric acid, hydrobromic acid, sulfuric acid, and the like, to afford the compound of Formula (13). Preferably, the reaction is carried out with sodium hydroxide in benzyl alcohol followed by hydrogenation in the presence of $Pd(OH)_2/C$ and sulfuric acid.

The process of the present invention in its second aspect is outlined in Scheme 2. Thus, a compound of Formula (4), prepared as described in Scheme 1, is reacted with a compound of Formula (20) wherein R and M are as defined above and a compound of Formula (7) with removal of water with the aid of a chemical drying agent such as, for example, molecular sieves and the like or with the aid of a Dean-Stark water trap or using azeotropic distillation with a suitable solvent such as, for example tetrahydrofuran, toluene, and the like, to afford a compound of Formula (8) wherein $R^1$ is as defined above. Preferably, the reaction is carried out with a compound of Formula (20) wherein R is $PhCH_2$ and M is sodium in the presence of activated 3A molecular seives in tetrahydrofuran.

The process of the present invention in its third aspect is outlined in Scheme 3. Thus, a compound of Formula (11) is reacted with an acetal of Formula (15) wherein $R^5$ and $R^5a$ are independently the same or different and are, methyl, ethyl, or —$(CH_2)_n$— wherein n is an integer of 2 to 4, and R is as defined above in the presence of an acid such as, for example, hydrochloric acid, pyridinium p-toluenesulfonate, p-toluenesulfonic acid and the like in a solvent such as, for example, toluene, dichloromethane, methyl tertiary butyl ether, and the like, followed by the addition of an aldehyde corresponding to the previous acetal of Formula (15) in the presence of a strong base such as, for example, a non-nucleophilic base, for example, potassium tertiary butoxide, potassium bis(trimethylsilyl) amide, 1,8-diazabicyclo[5.4.0]undec-7-ene and the like, to afford a compound of Formula (14) wherein $R^1$ and R are as defined above. Preferably, the reaction is carried out with benzaldehyde dimethyl acetal in toluene in the presence of p-toluenesulfonic acid followed by the addition of benzaldehyde and potassium tertiary butoxide in tetrahydrofuran.

A compound of Formula (14) is reacted with hydrogen in the presence of a catalyst such as, for example, palladium on carbon or platinum on carbon and the like in the presence of an acid such as, for example, hydrochloric acid and the like in a solvent such as, for example, toluene, tetrahydrofuran, methyl tertiary butyl ether, ethyl acetate, and the like, and an alcohol, such as, for example, methanol, ethanol, and the like, to afford a compound of Formula (13). Preferably, the reaction is carried out in toluene in the presence of platinum on carbon in the presence of methanol in the presence of hydrochloric acid.

Optionally, a compound of Formula (14) is reacted with an acid such as, for example, hydrochloric acid, pyridinium p-toluenesulfonate, p-toluenesulfonic acid, and the like, in a solvent such as, for example, toluene, dichloromethane, methyl tertiary butyl ether, and the like to afford the compound of Formula (13). Preferably, the reaction is carried out in methylene chloride in the presence of p-toluenesulfonic acid.

Alternatively, a compound of Formula (11) is reacted with an acid, such as, for example, hydrochloric acid, hydrobromic acid, p-toluenesulfonic acid, and the like, in a non-nucleophilic solvent, such as, for example, toluene, acetonitrile, methyl tertiary butyl ether, tetrahydrofuran, and the like, to afford a compound of Formula (13). Preferably, the reaction is carried out in toluene in the presence of p-toluenesulfonic acid.

The process of the present invention in its fourth aspect is outlined in Scheme 4. Thus, a compound of Formula (10)

wherein $R^1$ is as defined above is reacted with one molar equivalent of hydrogen in the presence of a catalyst using the methodology described above for the conversion of a compound of Formula (10) to a compound of Formula (11) to afford either a compound of Formula (18) or Formula (18a) wherein $R^1$ is as defined above or a mixture thereof. A mixture of compounds of Formula (18) and (18a) may be separated using conventional methodology, such as, for example, chromatography and the like. Preferably, a mixture of compounds of Formula (18) and (18a) is separated using HPLC.

A compound of Formula (18) or (18a) or a mixture thereof is reacted with hydrogen in the presence of a catalyst as described above for preparing a compound of Formula (11) to afford a compound of Formula (11b) wherein $R^1a$ is as defined above. Preferably, the reaction is carried out using at least one molar equivalent of hydrogen.

The compound of Formula (13) can be converted to atorvastatin calcium (19) using the procedures disclosed in U.S. Pat. No. 5,273,995 and 5,969,156.

The following nonlimiting examples illustrate the inventors' preferred methods for preparing the compounds of the invention.

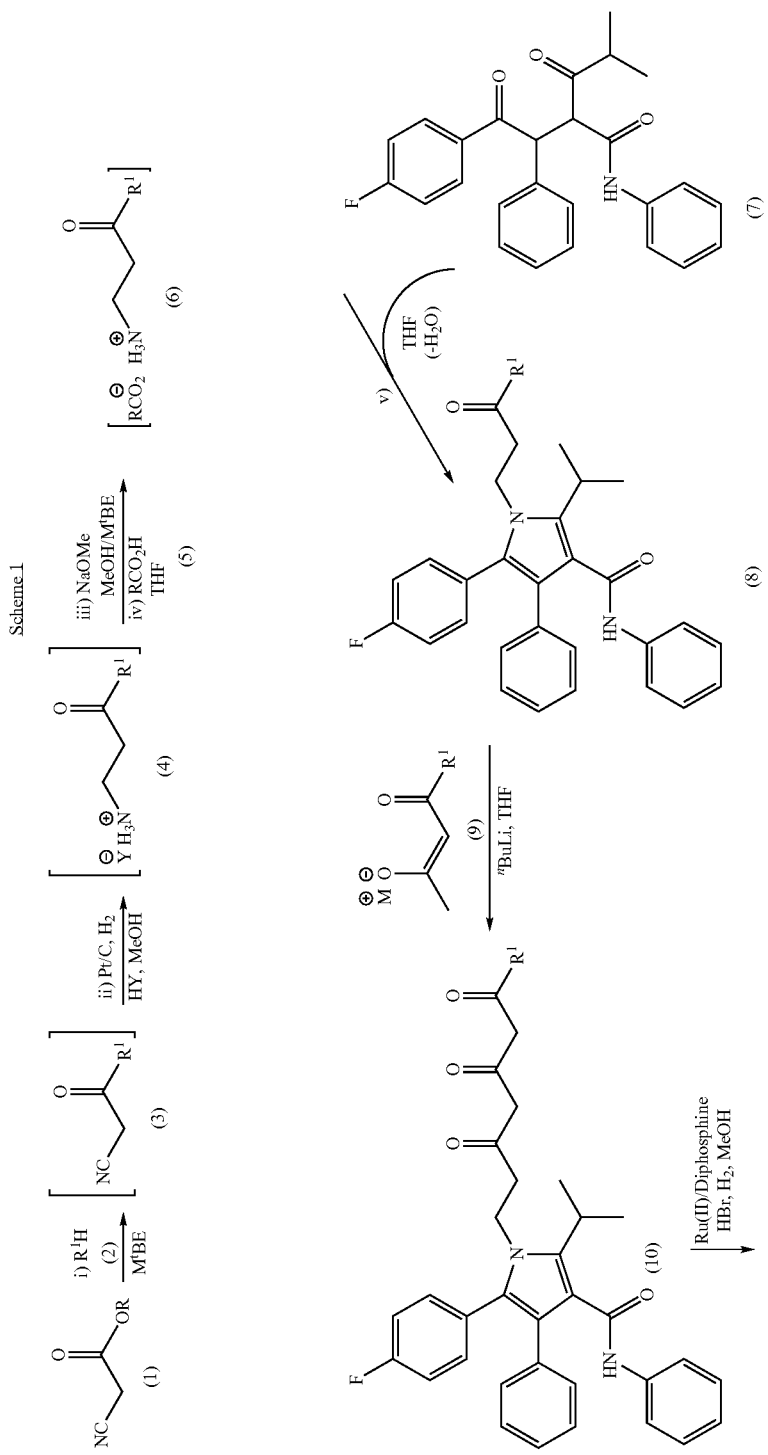

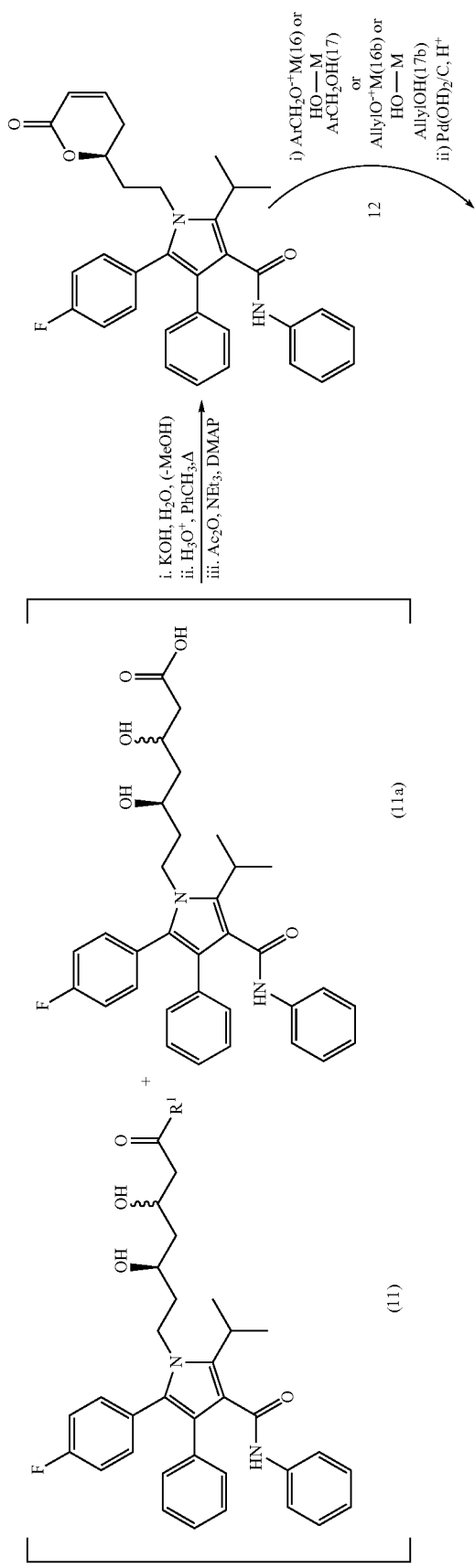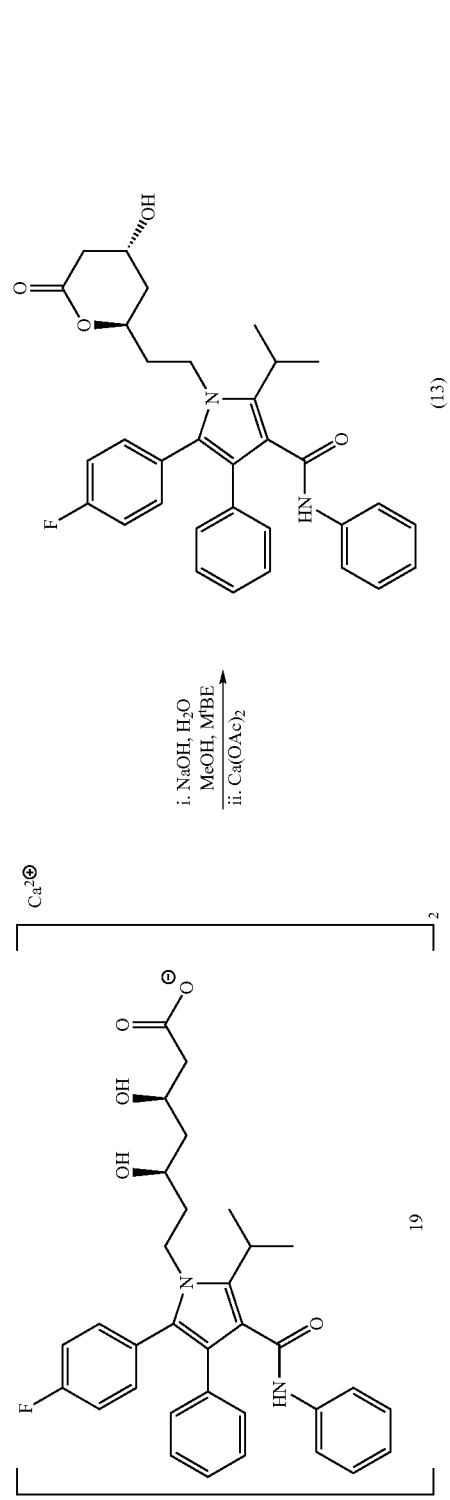

Scheme 2
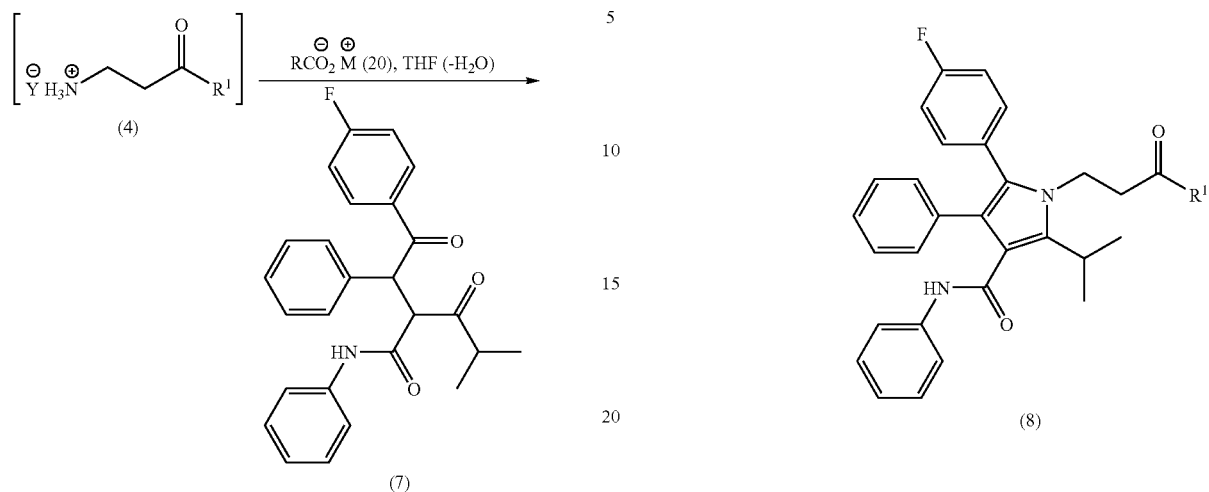
Scheme 3
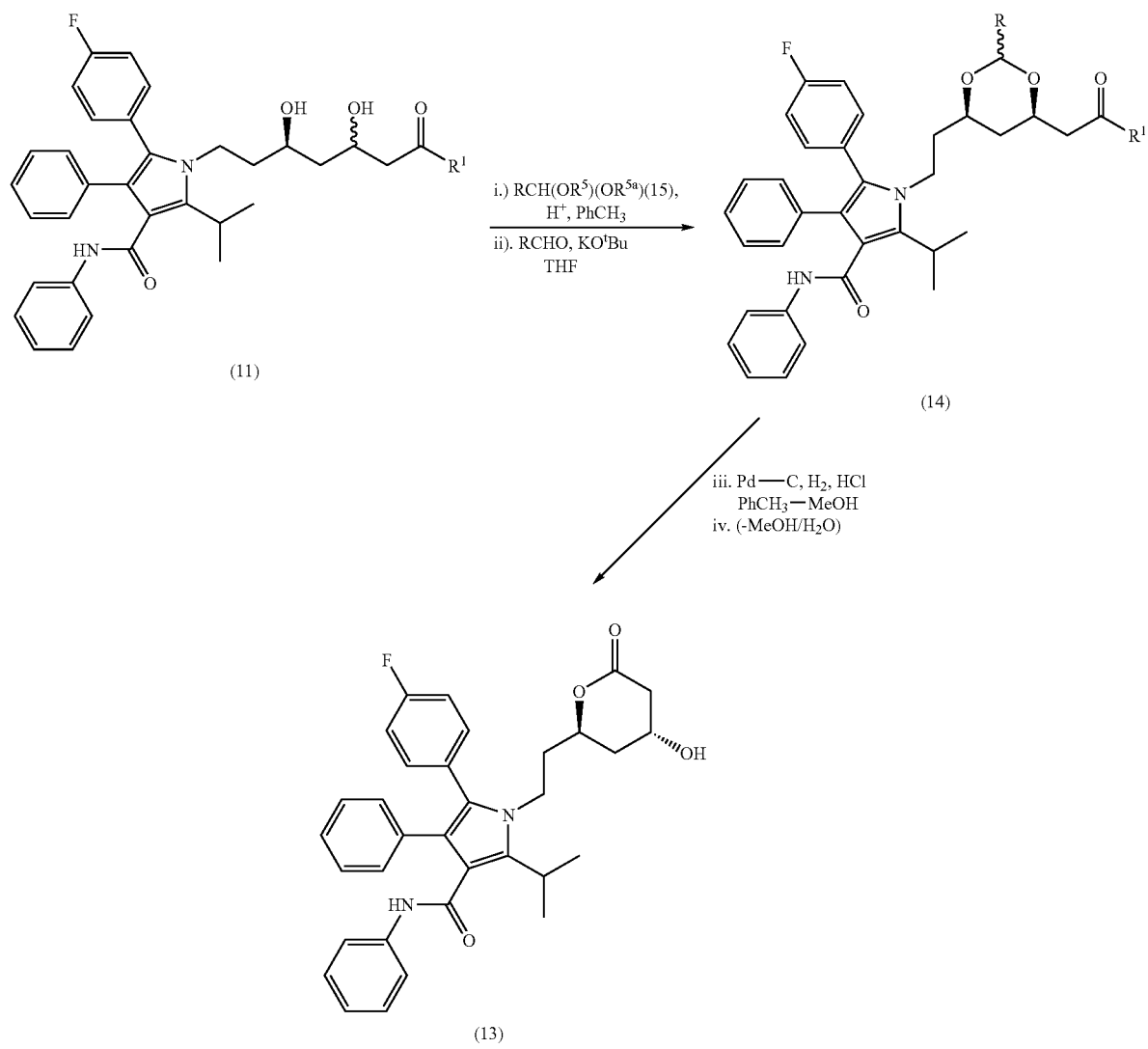

Scheme 4

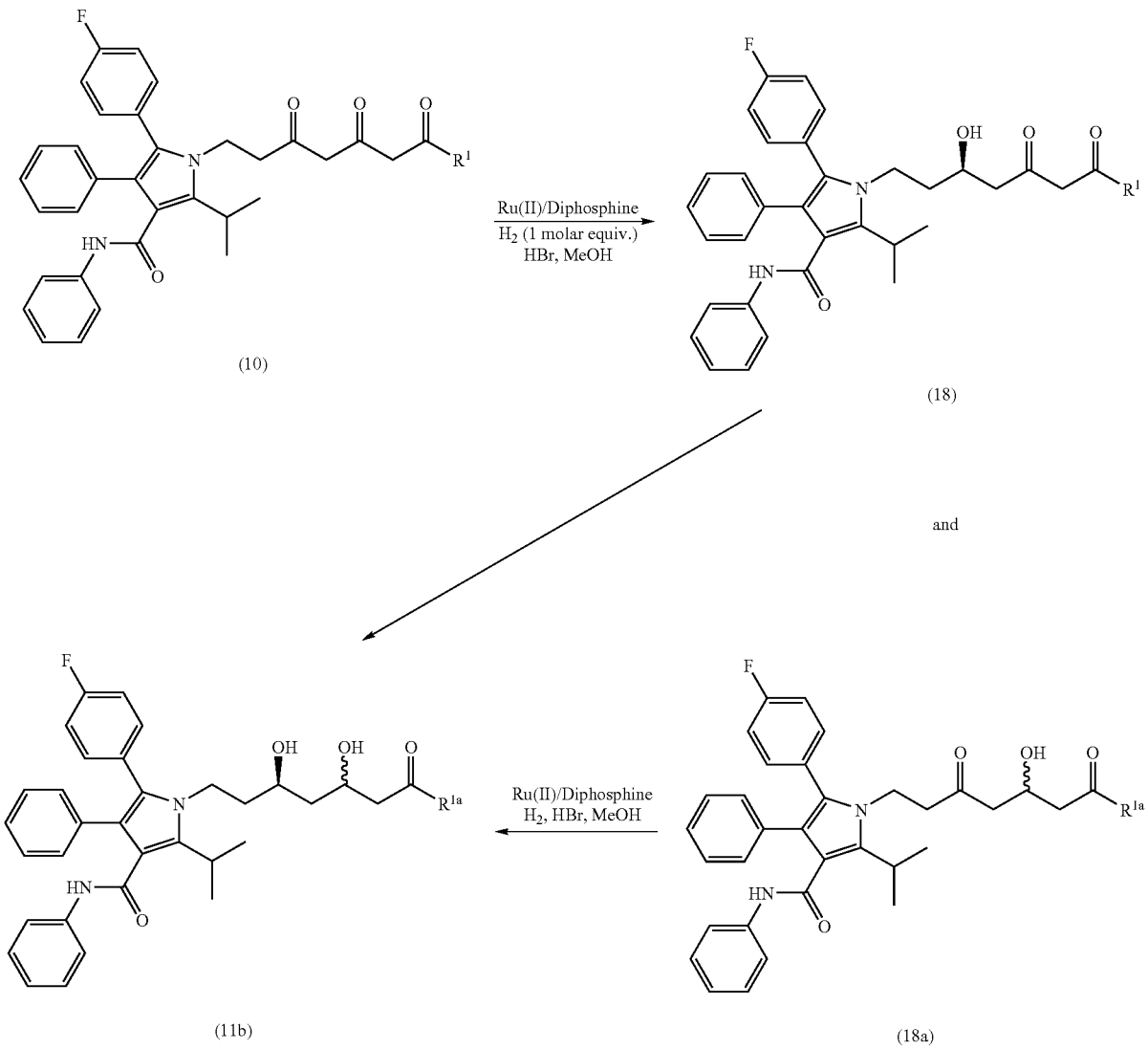

EXAMPLE 1

5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide Step 1: 3-Morpholin-4-yl-3-oxo-propionitrile

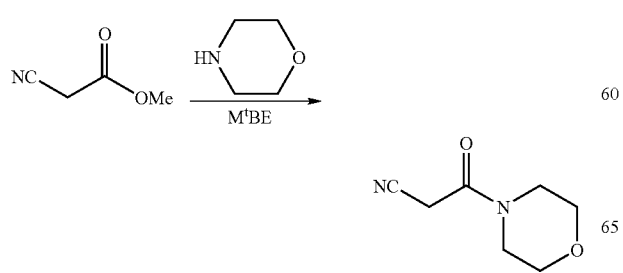

A nitrogen inerted reactor equipped with reflux condenser, nitrogen inlet and mechanical stirring is charged with morpholine (1.2 mol), methyl cyanoacetate (1.0 mol) and MtBE (52 mL). The homogeneous solution is heated to ca. 55° C. and stirred at that temperature for 12 to 18 hours. MtBE (33 mL) is added over ca. 15 minutes, and the solution is slowly cooled below 50° C. where nucleation becomes evident. Additional MTBE (66 μL) is added over a 1-hour period. During this time, the reaction is allowed to cool to near ambient temperature. After complete MtBE addition, the reaction is cooled with stirring to ca. 0° C. The resulting precipitate is collected via filtration and the cake is washed with additional MtBE (ca. 40 mL). The solid is dried under vacuum at ca. 45° C. to provide 3-morpholin-4-yl-3-oxo-propionitrile (139 g). This material is used in subsequent steps without further purification.

m/z (APCI(m+1)) 154.9; calcd for $C_7H_{10}N_2O_2$ 154.07.

Step 2: 3-Amino-1-morpholin-4-yl-propan-1-one; hydrochloride

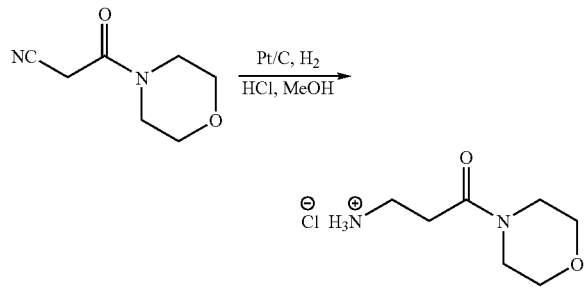

A nitrogen inerted reactor is charged with 5% Pt-C (43 g; 58% water-wet) followed by 3-morpholin-4-yl-3-oxo-propionitrile (2.8 mol). A solution of MeOH (3.4 L) and 12N HCl (3.08 mol) is added at such a rate as to maintain an internal temperature of ca. 25° C. The vessel and its contents are degassed via three $N_2$ pressure purges (50 psi). The atmosphere is switched to hydrogen via three $H_2$ pressure purges (50 psi), and the reaction is stirred vigorously at ca. 25° C. under a sustained pressure of hydrogen (50 psi) for ca. 24 hours. The $H_2$ pressure is released and replaced with $N_2$. The reaction is passed through filter agent, which is subsequently washed with MeOH (500 mL). The reaction is concentrated in vacuo to a volume of ca. 1.4 L, and IPA (2.2 L) is added. The reaction mixture is cooled to 0° C. and filtered. The filter cake is washed with MtBE (500 mL) and dried under vacuum at ca. 30° C. to provide 3-amino-1-morpholin-4-yl-propan-1-one, hydrochloride as a white solid (439 g). This material is used in subsequent steps without further purification.

$^1$H NMR (400 MHz, DMSO) δ 2.72 (t, 2H, J=6.78), 2.96 (t, 2H, J=6.77), 3.83–3.44 (m, 2H), 3.52–3.58 (m, 2H), 8.08 (bs, 3H).

$^{13}$C NMR (100 MHz, DMSO) δ 168.4, 65.9, 45.1, 41.45, 35.1, 29.6.

Free base: m/z (APCI(m+1)) 159.2; calcd for $C_7H_{14}N_2O_2$ 158.11.

Step 3: 3-Amino-1-morpholin-4-yl-propan-1-one; compound with phenylacetic acid

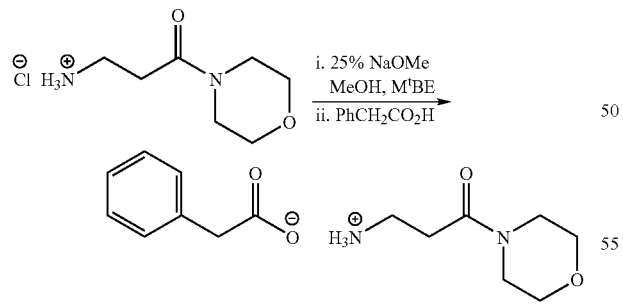

A reactor is charged with 3-amino-1-morpholin-4-yl-propan-1-one; hydrochloride (765 mmol). MeOH (380 mL) is added, and the mixture is stirred vigorously at room temperature for ca. 10 minutes. MtBE (380 mL) is added and the resulting slurry is cooled to −10° C., where a 25% (w/w) MeOH solution of NaOMe (765 mmol) is added slowly via addition funnel at such a rate as to maintain an internal temperature of ca. −10° C. The resulting suspension is stirred vigorously under a $N_2$ atmosphere as it is allowed to warm to 0° C. Solids are removed via filtration, rinsing with additional MtBE (50 mL). Solvent is removed in vacuo to provide the free base as a crude oil that is taken up in MtBE (600 mL). The mixture is cooled with vigorous agitation to ca. 0° C., where phenylacetic acid (765 mmol) is added slowly as a solution in MtBE (300 mL). The reaction mixture is stirred an additional 10 minutes after complete addition, during which time the product precipitates out of solution. The solids are collected via filtration, washed with additional MtBE (100 mL) and dried under vacuum at <40° C. to provide 3-amino-1-morpholin-4-yl-propan-1-one; compound with phenylacetic acid (191 g). This material is carried on to subsequent steps without further purification, or optionally, it can be re-precipitated from MtBE.

$^1$H NMR (400 MHz, DMSO) δ 2.55 (t, 2H, J=6.78), 2.86 (t, 2H, J=6.78) 3.62 (t, 2H), 3.42 (t, 2H), 6.22 (bs, 3H), 7.25–7.12 (m, 5H).

$^{13}$C NMR (100 MHz, DMSO) δ 174.2, 169.0, 138.2, 129.2, 127.8, 125.5, 66.0, 45.2, 44.4, 41.4, 35.7, 31.6.

Step 4: 5-(4-Fluorophenyl)-2-isopropyl-1-(3-morpholin-4-yl-3-oxo-propyl)-4-phenyl-1H-pyrrole-3-carboxylic acid phenylamide Method A

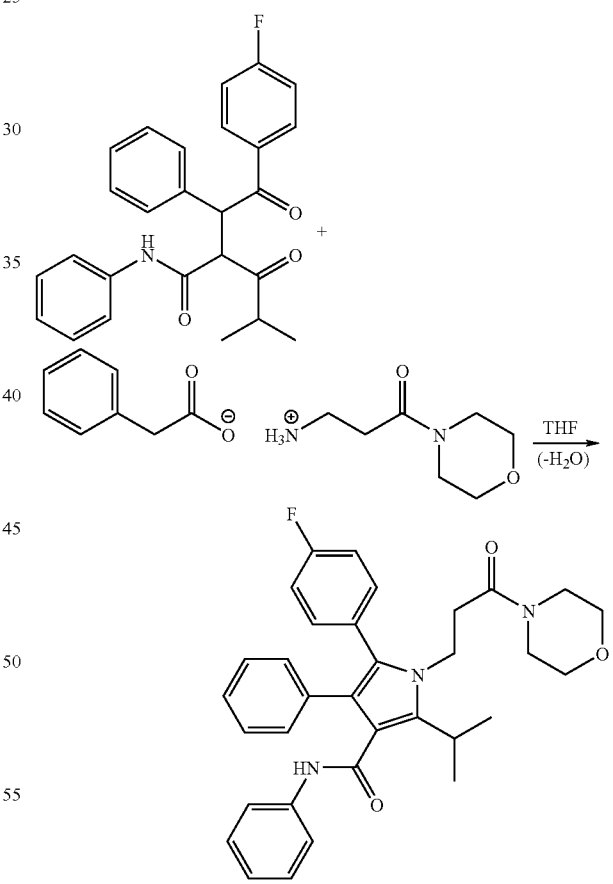

A nitrogen inerted reactor, equipped with a suitable reflux condenser and soxhlet extractor containing freshly activated 3A molecular sieves (4–8 mesh; 97.2 g), is charged with 3-amino-1-morpholin-4-yl-propan-1-one, compound with phenylacetic acid (765 mmol) and 2-[2-(4-fluorophenyl)-2-oxo-1-phenyl-ethyl]-4-methyl-3-oxo-pentanoic acid phenylamide (450 mmol). THF (360 mL) is added, and the resulting solution is stirred vigorously as the reaction is heated at reflux temperature for ca. 24 hours, during which time the product begins to precipitate. Half-saturated aqueous NaHCO$_3$ (100 mL) is added, and the reaction mixture is cooled with continued stirring to ca. 0° C. MtBE (100 mL) is added, and the solids are collected via filtration. The solid is washed with distilled water (100 mL) and MtBE (2×100 mL), collected, and dried under vacuum at <50° C. to afford 5-(4-fluorophenyl)-2-isopropyl-1-(3-morpholin-4-yl-3-oxo-propyl)-4-phenyl-1H-pyrrole-3-carboxylic acid phenylamide as a white solid (194 g). This material is carried on to subsequent steps without further purification.

m/z (APCI(m$^{-1}$)) 538.2; (APCI(m+1) 540.2; calcd for C$_{33}$H$_{34}$FN$_3$O$_3$ 539.26.

Method B

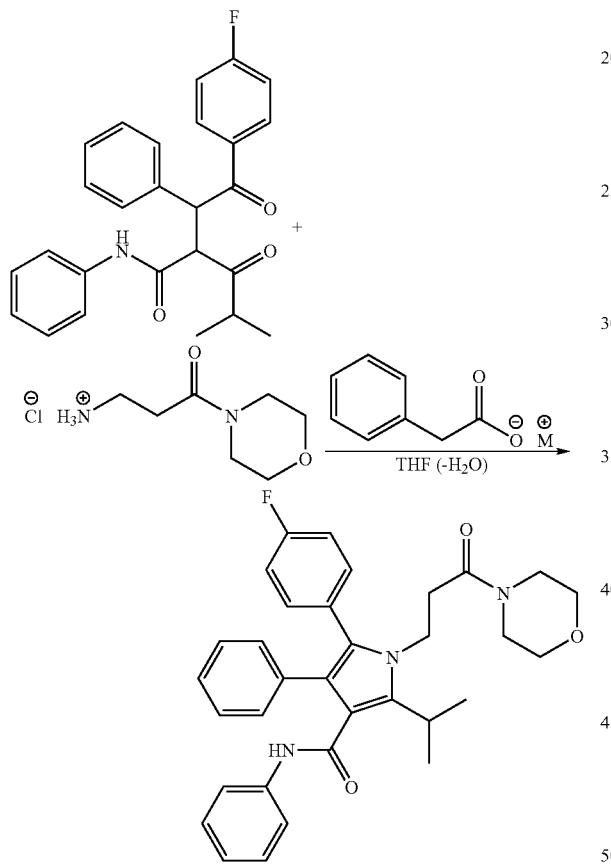

A nitrogen inerted reactor, equipped with a suitable reflux condenser and soxhlet extractor containing freshly activated 3A molecular sieves (4–8 mesh; 36 g), is charged with 3-amino-1-morpholin-4-yl-propan-1-one hydrochloride (170 mmol), phenylacetic acid sodium salt (170 mmol) and 2-[2-(4-fluorophenyl)-2-oxo-1-phenyl-ethyl]-4-methyl-3-oxo-pentanoic acid phenylamide (100 mmol). THF (150 mL) is added, and the resulting solution is stirred vigorously as the reaction is heated at reflux temperature for ca. 24 hours, during which time the product begins to precipitate. Aqueous NaHCO$_3$ (100 mL) is added slowly, and the reaction mixture is cooled with continued stirring to ca. 0° C. MtBE (100 ML) is added, and the solids are collected via filtration. The yellow-colored solid is washed with distilled water (15 mL) and MtBE (2×15 mL), collected, and dried under vacuum at <50° C. to afford 5-(4-fluorophenyl)-2-isopropyl-1-(3-morpholin-4-yl-3-oxo-propyl)-4-phenyl-1H-pyrrole-3-carboxylic acid phenylamide as a white solid (42.1 g). This material is carried on to subsequent steps without further purification.

m/z (APCI(m−1)) 538.2; (APCI(m+1) 540.2; calcd for C$_{33}$H$_{34}$FN$_3$O$_3$ 539.26.

Method C

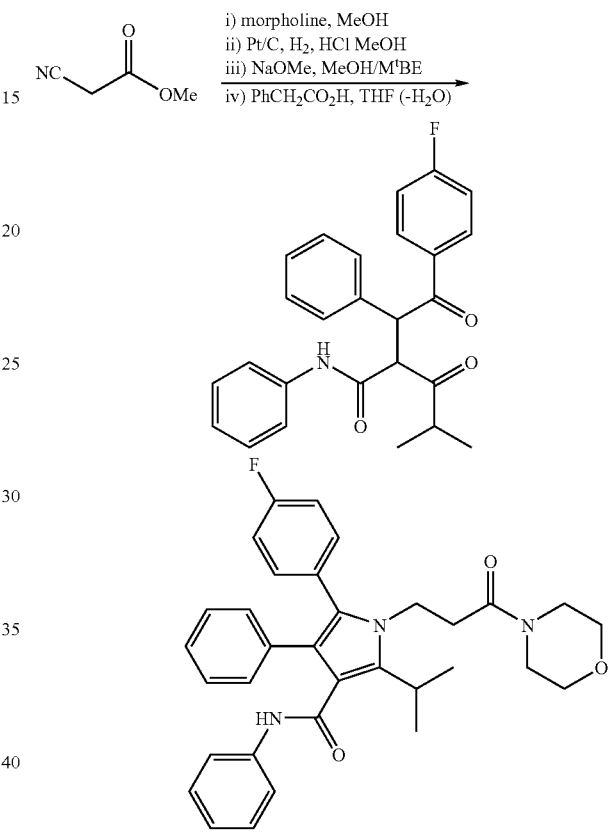

A nitrogen inerted reactor equipped with reflux condenser, nitrogen inlet and mechanical stirring is charged with morpholine (1.2 mol), methyl cyanoacetate (1.0 mol), and MtBE (52 mL). The homogeneous solution is heated to ca. 55° C. and stirred at that temperature for 12 to 18 hours. MtBE (33 mL) is added over ca. 15 minutes, and the solution is slowly cooled below 50° C. until nucleation becomes evident. Additional MtBE (66 mL) is added over a 1-hour period. During this time, the reaction is allowed to cool to near ambient temperature. After complete MtBE addition, the reaction is cooled with stirring to ca. 0° C. The resulting precipitate is collected via filtration and the cake is washed with additional MtBE (40 mL). The crude 3-morpholin-4-yl-3-oxo-propionitrile is taken up in MeOH (2 L) and transferred to a nitrogen inerted pressure reactor that has been charged with 5% Pt-C (55 g; 58% water-wet). HCl (12 N, 1.1 mol) is added at such a rate as to maintain an internal temperature of ca. 25° C. The vessel and its contents are degassed via three N$_2$ pressure purges (50 psi). The atmosphere is switched to hydrogen via three H$_2$ pressure purges (50 psi), and the reaction is stirred vigorously at ca. 25° C. under a sustained pressure of hydrogen (50 psi) for ca. 24 hours. The H$_2$ pressure is released and replaced with N$_2$. The reaction is passed through filter agent, which is subsequently washed with MeOH (500 mL). The reaction is concentrated to a MeOH-wet solid, which is reslurried in IPA (100 mL). The slurry is cooled to 0° C. and filtered. The filter cake is washed with cold (0° C.) IPA (75 mL) and reslurried in MeOH (500 ML) and MtBE (500 mL). The slurry is cooled with agitation to −10C where a 25% (w/w) solution of NaOMe in MeOH (1 mol) is added dropwise at such a rate as to maintain an internal reaction temperature of ≦−5° C. The resulting suspension is filtered to afford a clear solution of free base. The solvent is removed in vacuo to provide a crude oil that is taken up in THF (450 mL) and cooled to ca. 0° C. This solution is transferred into a nitrogen inerted reactor that contains phenylacetic acid (1.0 mol) and 2-[2-(4-fluorophenyl)-2-oxo-1-phenyl-ethyl]-4-methyl-3-oxo-pentanoic acid phenylamide (590 mmol). The reactor is equipped with a suitable reflux condenser and soxhlet extractor containing freshly activated 3A molecular sieves (4–8 mesh; 125 g). The resulting solution is stirred vigorously as the reaction is refluxed under a N₂ atmosphere for ca. 24 hours, during which time the product begins to precipitate. Half-saturated aqueous NaHCO₃ (130 mL) is added slowly, and the reaction mixture is cooled with continued stirring to ca. 0° C. MtBE (130 mL) is added, and the solids are collected via filtration. The solid is washed with distilled water (130 mL) and MtBE (2×130 mL), collected, and dried under vacuum at <50° C. to afford 5-(4-fluorophenyl)-2-isopropyl-1-(3-morpholin-4-yl-3-oxo-propyl)-4-phenyl-1H-pyrrole-3-carboxylic acid phenylamide as a white solid (223 g). This material is carried on to subsequent steps without further purification.

m/z (APCI(m−1)) 538.2; (APCI(m+1) 540.2; calcd for C$_{33}$H$_{34}$FN$_3$O$_3$ 539.26.

Step 5: 7-[2-(4-Fluorophenyl)-5-isopropyl-3-phenyl-4-phenylcarbamoyl-pyrrol-1-yl]-3,5-dioxo-heptanoic acid, ethyl ester Method A

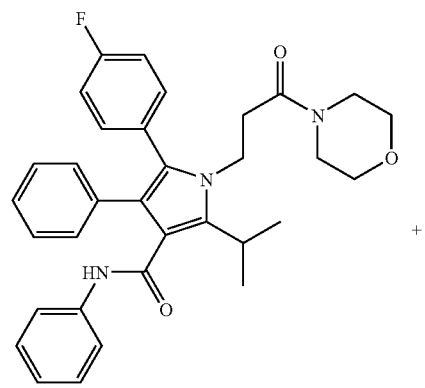

+

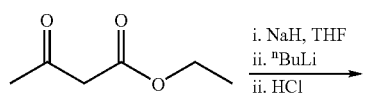

i. NaH, THF
ii. ⁿBuLi
iii. HCl

-continued

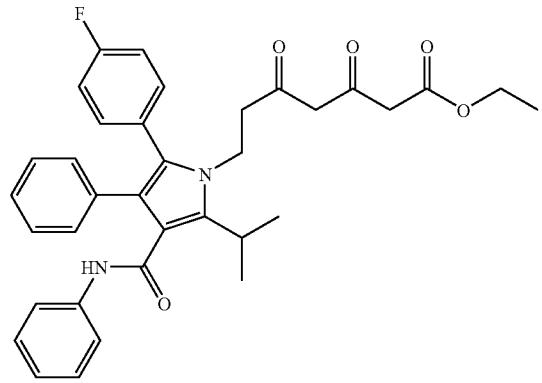

A dry, nitrogen inerted reactor is charged with sodium hydride (300 mmol). Anhydrous THF (150 mL) is added and the resulting mixture is cooled under nitrogen to ca. −20° C. Ethyl acetoacetate (307 mmol) is added at such a rate as to maintain an internal reaction temperature of ≦−10° C. The addition is followed by a T1F rinse (30 mL) and the resulting solution is stirred for approximately 45 minutes at ≦−10° C. The temperature is allowed to cool to ca. −18° C. A 10.0 M solution of n-BuLi in hexanes (300 mmol) is added at such a rate as to maintain an internal reaction temperature of ≦−4° C. The addition is followed by a THF rinse (30 mL) and the resulting orange solution is stirred for about 90 minutes at ≦−4° C. The temperature is allowed to cool to ca. −25° C. To the solution of dienolate is added 5-(4-fluorophenyl)-2-isopropyl-1-(3-morpholin-4-yl-3-oxo-propyl)-4-phenyl-1H-pyrrole-3-carboxylic acid phenylamide (74 mmol), and the resulting slurry is stirred at ca. −23° C. for 20 hours. The reaction is quenched into a mixture of 18% aqueous HCl (898 mmol) and MTBE (20 mL) at such a rate as to maintain an internal reaction temperature of ≦−2° C. The reactor and transfer system is rinsed with THF (30 mL) and transferred to the reaction mixture. The two-phase solution is allowed to warm to ca. 20° C. with stirring. The mixture is transferred to a separatory funnel, and the phases are allowed to separate. The organic layer is washed with water (33 mL) and saturated aqueous NaCl (33 mL). All aqueous layers are back-extracted with MtBE (40 mL). The two organic layers are combined and concentrated in vacuo to a crude oil maintaining an internal batch temperature of ≦60° C. EtOH (24 ML) is added to the oil and, again, the mixture is concentrated in vacuo. EtOH (330 mL) and water (33 mL) are immediately added to the resulting oil, and the solution of product is allowed to stand at ≦10° C. for ca. 14 hours. The resulting solid is collected, washed with cold 20% aqueous EtOH (100 mL) and dried in vacuo to afford 7-[2-(4-fluorophenyl)-5-isopropyl-3-phenyl-4-phenylcarbamoyl-pyrrol-1-yl]-3,5-dioxo-heptanoic acid, ethyl ester (35.6 g) as a white solid. This material is carried on to subsequent steps without further purification, or optionally, it can be re-precipitated from IPA/H₂O.

HRMS m/z (ESI(m−1)) 581.2463; calcd for C$_{35}$H$_{35}$FN$_2$O$_5$ 582.2530.

In a process analogous to Step 5 METHOD A, by substituting the appropriate ester or amide of acetoacetic acid for ethyl acetoacetate, one obtains the following compounds:

7-[2-(4-Fluorophenyl)-5-isopropyl-3-phenyl-4-phenylcarbamoyl-pyrrol-1-yl]-3,5-dioxo-heptanoic acid, tert-butyl ester.

HRMS m/z (ESI(m−1)) 609.2772; APCI(m+1) 611.3; calcd for $C_{37}H_{39}FN_2O_5$ 610.2843.

7-[2-(4-Fluorophenyl)-5-isopropyl-3-phenyl-4-phenylcarbamoyl-pyrrol-1-yl]-3,5-dioxo-heptanoic acid, isopropyl ester.

m/z (DCI(m+1)) 597; calcd for $C_{36}H_{37}FN_2O_5$ 596.27.

7-[2-(4-Fluorophenyl)-5-isopropyl-3-phenyl-4-phenylcarbamoyl-pyrrol-1-yl]-3,5-dioxo-heptanoic acid, methyl ester.

m/z (DCI(m+1)) 569; calcd for $C_{34}H_{33}FN_2O_5$ 568.24.

7-[2-(4-Fluorophenyl)-5-isopropyl-3-phenyl-4-phenylcarbamoyl-pyrrol-1-yl]-3,5-dioxo-heptanoic acid, morpholino amide.

HRMS m/z (ESI(m−1)) 622.2715; calcd for $C_{37}H_{38}FN_3O_5$ 623.2795.

7-[2-(4-Fluorophenyl)-5-isopropyl-3-phenyl-4-phenylcarbamoyl-pyrrol-1-yl]-3,5-dioxo-heptanoic acid, N,N-dimethyl amide.

m/z (DCI(m+1)) 582; calcd for $C_{35}H_{36}FN_3O_4$ 581.27.

Method B

7-[2-(4-Fluorophenyl)-5-isopropyl-3-phenyl-4-phenylcarbamoyl-pyrrol-1-yl]-3,5-dioxo-hep acid, tert-butyl ester

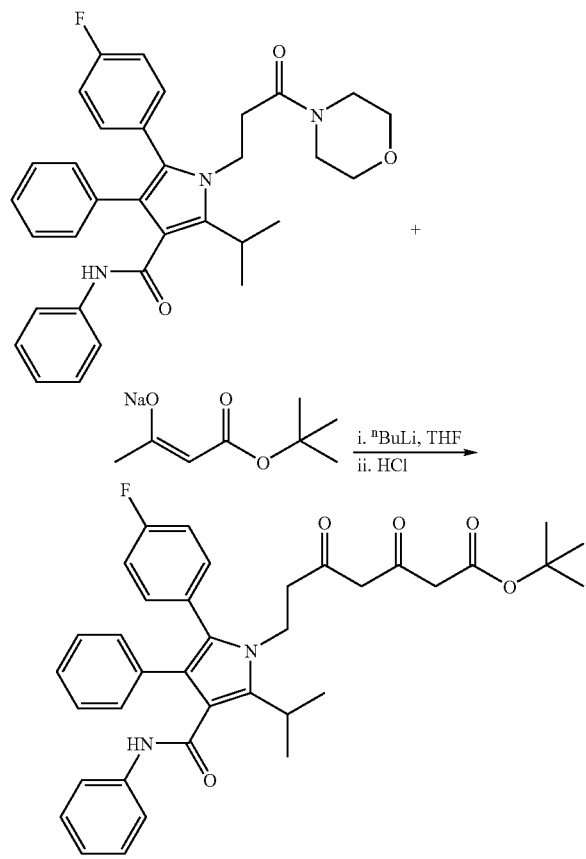

A nitrogen inerted reactor is charged with the sodium salt of tert-butyl acetoacetate (100 mmol). Anhydrous toluene (71.5 mL) and THF (8.2 mL, 101 mmol) are added, and the resulting solution is cooled under a positive pressure of nitrogen to ca. −10° C. A 10 M hexanes solution of n-BuLi (104 mmol) is added at such a rate as to maintain an internal reaction temperature of <1° C. The resulting solution is stirred an additional 20 to 30 minutes after complete addition as the temperature is allowed to cool to ca. −6° C.

Meanwhile, 5-(4-fluorophenyl)-2-isopropyl-1-(3-morpholin-4-yl-3-oxo-propyl)-4-phenyl-1H-pyrrole-3-carboxylic acid phenylamide (25 mmol) is charged to a second nitrogen inerted reactor. Anhydrous THF (50 mL) is added at room temperature, and the resulting slurry is cooled to ca. −10° C. and stirred for 15 to 90 minutes. The solution of dienolate is added to the slurry of morpholine amide at such a rate as to maintain an internal reaction temperature ca. −5° C. Following this addition, the slurry is stirred at ca. −5° C. for >2 hours. Water (35 mL) is added with vigorous agitation at such a rate as to maintain an internal reaction temperature of <0° C. Concentrated 37% hydrochloric acid (19.0 mL, 229 mmol) is added at such a rate as to maintain an internal reaction temperature of ≦0° C. The two-layered reaction mixture is vacuum distilled, removing >50% of the organic solvents. The distillation is stopped and the lower aqueous layer is discarded. Water (55 mL) is added and the vacuum distillation is continued until a majority of the organic solvents are removed. [Note: It is preferable to drain and replace the aqueous layer before initiating the vacuum distillation.] IPA (100 mL) is added followed by water (100 mL). The mixture is stirred for >6 hours, allowing for solidification of the product. The solid is collected via filtration, and the cake is washed with pre-mixed 1:1 IPA:$H_2O$. The resulting solid is dried in vacuo at 35° C. to provide 7-[2-(4-fluorophenyl)-5-isopropyl-3-phenyl-4-phenylcarbamoyl-pyrrol-1-yl]-3,5-dioxo-heptanoic acid, tert-butyl ester (14.1 g) as a white solid. This material is carried on to subsequent steps without further purification, or optionally, it can be re-precipitated from toluene.

HRMS m/z (ESI(m−1)) 609.2772; APCI(m+1) 611.3; calcd for $C_{37}H_{39}FN_2O_5$ 610.2843.

In a process analogous to Step 5 METHOD B, by substituting the sodium salt of the appropriate ester or amide of acetoacetic acid for the sodium salt of tert-butyl acetoacetate, one obtains the following compounds:

7-[2-(4-Fluorophenyl)-5-isopropyl-3-phenyl-4-phenylcarbamoyl-pyrrol-1-yl]-3,5-dioxo-heptanoic acid, ethyl ester.

HRMS m/z (ESI(m−1)) 581.2463; calcd for $C_{35}H_{35}FN_2O_5$ 582.2530.

7-[2-(4-Fluorophenyl)-5-isopropyl-3-phenyl-4-phenylcarbamoyl-pyrrol-1-yl]-3,5-dioxo-heptanoic acid, isopropyl ester.

m/z (DCI(m+1)) 597; calcd for $C_{36}H_{37}FN_2O_5$ 596.27.

7-[2-(4-Fluorophenyl)-5-isopropyl-3-phenyl-4-phenylcarbamoyl-pyrrol-1-yl]-3,5-dioxo-heptanoic acid, methyl ester.

m/z (DCI(m+1)) 569; calcd for $C_{34}H_{33}FN_2O_5$ 568.24.

7-[2-(4-Fluorophenyl)-5-isopropyl-3-phenyl-4-phenylcarbamoyl-pyrrol-1-yl]-3,5-dioxo-heptanoic acid, morpholino amide.

HRMS m/z (ESI(m−1)) 622.2715; calcd for $C_{37}H_{38}FN_3O_5$ 623.2795.

7-[2-(4-Fluorophenyl)-5-isopropyl-3-phenyl-4-phenylcarbamoyl-pyrrol-1-yl]-3,5-dioxo-heptanoic acid, N,N-dimethyl amide.

m/z (DCI(m+1)) 582; calcd for $C_{35}H_{36}FN_3O_4$ 581.27.

Step 6: (5R)-7-[2-(4-Fluorophenyl)-5-isopropyl-3-phenyl-4-phenylcarbamoyl-pyrrol-1-yl]-3,5-dihydroxy-heptanoic acid, methyl ester Method A

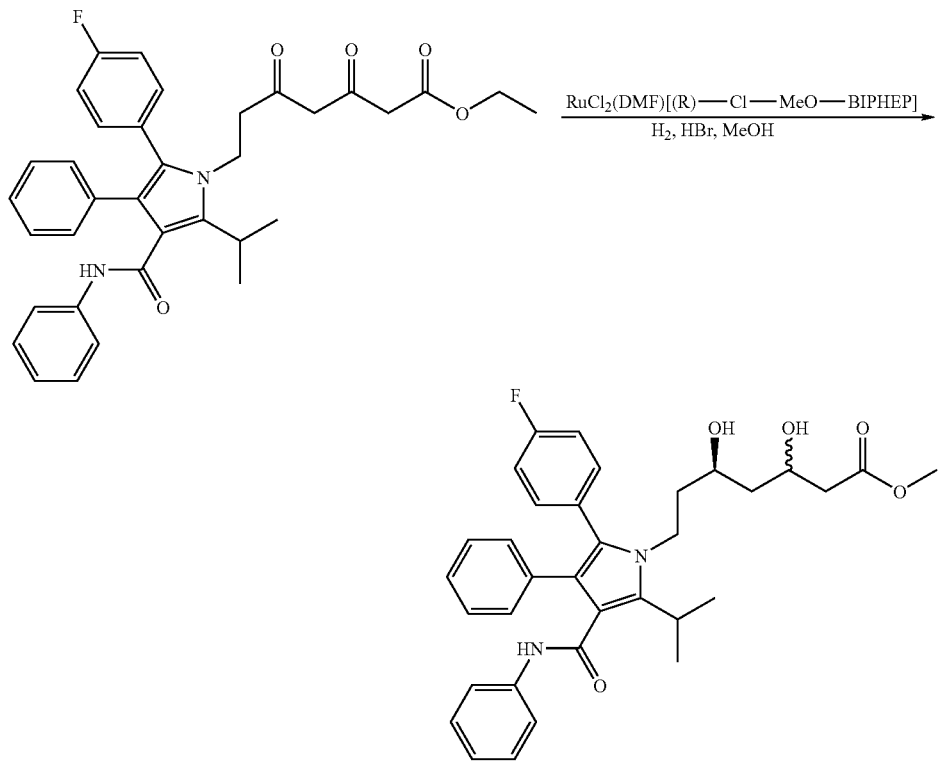

A nitrogen inerted pressure reactor is charged with 7-[2-(4-fluorophenyl)-5-isopropyl-3-phenyl-4-phenylcarbamoyl-pyrrol-1-yl]-3,5-dioxo-heptanoic acid, ethyl ester (100.0 mmol) and MeOH (250 mL). The resulting slurry is heated with stirring to ca. 55° C. to afford a homogeneous solution. The vessel and its contents are degassed via three 50 psi pressure purges with argon. Under a steady flow of argon, 1 M methanolic HBr (7.0 mmol) and the RuCl$_2$(DMF)$_n$[(R)-Cl—MeO-BIPHEP)] catalyst (0.5 mmol) are added, and the reactor is given an additional 50 psi pressure purge with argon. The atmosphere is switched to hydrogen via three 50 psi pressure purges. The reaction is stirred vigorously at 65° C. under a sustained pressure of hydrogen (50 psi) until hydrogen uptake ceases. The reaction is allowed to cool to ambient temperature, and the hydrogen pressure is released and replaced with nitrogen. The crude MeOH solution of (5R)-7-[2-(4-fluorophenyl)-5-isopropyl-3-phenyl-4-phenylcarbamoyl-pyrrol-1-yl]-3,5-dihydroxy-heptanoic acid, methyl ester is carried on to subsequent steps without purification, or optionally, it can be isolated via flash column chromatography on silica gel, eluting with ethyl acetate-heptane mixtures.

HPLC analysis (YMC ODS AQ S5; 1 mL/min; 30° C.; 254 μm: CH$_3$CN/H$_2$O, 60:40 (0–22 min) to 100:0 (27–37 min) to 60:40) indicated a syn:anti ratio of 1:1.5. Chiral HPLC analysis (Chiralcel OD-H column; 5% EtOH:Hexanes; $t_R$(3R,5R)=23.1 min./$t_R$(3R,5S)=18.0 min./$t_R$(3S,5S)=24.8 min./$t_R$(3S,5R)=19.9 min.) indicated an enantiomeric excess at C—S of >98%, favoring the (R) configuration.

m/z (DCI(m+1)) 573; calcd for C$_{34}$H$_{37}$FN$_2$O$_5$ 572.27.

In a process analogous to Step 6 METHOD A, using the appropriate alcoholic solvent in place of MeOH, one obtains the following compounds, for example:

(5R)-7-[2-(4-Fluorophenyl)-5-isopropyl-3-phenyl-4-phenylcarbamoyl-pyrrol-1-yl]-3,5-dihydroxy-heptanoic acid, ethyl ester.

m/z (DCI(m+1)) 587; calcd for C$_{35}$H$_{39}$FN$_2$O$_5$ 586.28.

Chiral HPLC analysis (Chiralcel OD-H column; 5% EtOH:Hexanes; $t_R$(3R,5R)=17.6 min./$t_R$(3R,5S)=14.7 min./$t_R$(3S,5S)=20.9 min./$t_R$(3S,5R)=15.9 min.) indicated an enantiomeric excess at C-5 of ≧98%, favoring the (R) configuration.

(5R)-7-[2-(4-Fluorophenyl)-5-isopropyl-3-phenyl-4-phenylcarbamoyl-pyrrol-1-yl]-3,5-dihydroxy-heptanoic acid, isopropyl ester.

m/z (DCI(m+1)) 601; calcd for C$_{36}$H$_{41}$FN$_2$O$_5$ 600.30.

In a process analogous to Step 6 METHOD A, using the appropriate ester or amide from Step 5 in a non-nucleophilic/non-coordinating solvent (e.g., toluene) in place of MeOH, and acetic acid in place of HBr, one can avoid transesterification and obtain the following compounds, for example:

(5R)-7-[2-(4-Fluorophenyl)-5-isopropyl-3-phenyl-4-phenylcarbamoyl-pyrrol-1-yl]-3,5-dihydroxy-heptanoic acid, tert-butyl ester.

m/z (APCI(m+1)) 615.3; calcd for C$_{37}$H$_{43}$FN$_2$O$_5$ 614.32.

(5R)-7-[2-(4-Fluorophenyl)-5-isopropyl-3-phenyl-4-phenylcarbamoyl-pyrrol-1-yl]-3,5-dihydroxy-heptanoic acid, morpholino amide.

m/z (APCI(m−1+HCO$_2$H)) 672.3; calcd for C$_{37}$H$_{42}$FN$_3$O$_5$ 627.31.

(5R)-7-[2-(4-Fluorophenyl)-5-isopropyl-3-phenyl-4-phenylcarbamoyl-pyrrol-1-yl]-3,5-dihydroxy-heptanoic acid, N,N-dimethyl amide.

m/z (APCI(m+1)) 586; calcd for C$_{35}$H$_{40}$FN$_3$O$_4$ 585.30.

In a process analogous to Step 6 METHOD A, using alternative Ru(II)-chiral diphosphine complexes in place of RuCl$_2$(DMF)$_n$[(R)-Cl—MeO-BIPHEP)] as the hydrogenation catalyst, one can obtain the identical products with varying enantiomeric excess at C-5. For example, in the reduction of 7-[2-(4-fluorophenyl)-5-isopropyl-3-phenyl-4-phenylcarbamoyl-pyrrol-1-yl]-3,5-dioxo-heptanoic acid, ethyl ester to (5R)-7-[2-(4-fluorophenyl)-5-isopropyl-3-phenyl-4-phenylcarbamoyl-pyrrol-1-yl]-3,5-dihydroxy-heptanoic acid, methyl ester proceeded as follows:

RuCl$_2$(DMF)$_n$[(R)-(+)-BINAP] complex provided product with 90% ee (favoring the (R) configuration) at C—S as determined by chiral HPLC analysis.

RuCl$_2$(DMF)$_n$[(R)-(+)-pTol-BINAP] complex provided product with 91% ee (favoring the (R) configuration) at C—S as determined by chiral HPLC analysis.

RuCl2(DMF)$_n$[(R)-(+)—C4-TunaPhos] complex provided product with 93% ee (favoring the (R) configuration) at C—S as determined by chiral HPLC analysis.

RuCl$_2$(DMF)$_n$[(R)-(+)—C2-TunaPhos] complex provided product with 98% ee (favoring the (R) configuration) at C—S as determined by chiral HPLC analysis.

RuCl$_2$(DMF)$_n$[(S)-(−)-MeO-BIPHEP] complex provided product with 95% ee (favoring the (S) configuration) at C—S as determined by chiral HPLC analysis.

RuCl$_2$[(R)-(+)-Cl—MeO-BIPHEP] (NEt$_3$)$_n$ complex provided product with ≧98% ee (favoring the (R) configuration) at C-s as determined by chiral HPLC analysis.

RuCl$_2$[(R)-(+)-BINAP] (NEt3)$_n$ complex provided product with 91% ee (favoring the (R) configuration) at C-s as determined by chiral HPLC analysis.

RuCl$_2$[(R)-(+)-pTol-BINAP] (NEt3)$_n$ complex provided product with 91% ee (favoring the (R) configuration) at C-s as determined by chiral HPLC analysis.

[Ru(TFA)$_2$((R)-(+)-Cl—MeO-BIPHEP)]$_n$ complex provided product with ≧98% ee (favoring the (R) configuration) at C-s as determined by chiral HPLC analysis.

[Ru(TFA)$_2$((R)-(+)-BINAP)]$_n$ complex provided product with 90% ee (favoring the (R) configuration) at C—S as determined by chiral HPLC analysis.

Method B

A nitrogen inerted pressure reactor is charged with benzene ruthenium (II) chloride dimer (11 mg) and (R)-(+)-C2-TunaPhos (26 mg). The reactor is given a pressure purge with N$_2$ and N$_2$-sparged MeOH (1.0 mL) is added via syringe. The resulting mixture is thoroughly purged with N$_2$ and stirred at 25° C. for 30 minutes. A solution of 7-[2-(4-fluorophenyl)-5-isopropyl-3-phenyl-4-phenylcarbamoyl-pyrrol-1-yl]-3,5-dioxo-heptanoic acid, tert-butyl ester (0.5 g) in N$_2$-sparged MeOH (4.5 mL) is added to the reactor via syringe, and the resulting mixture is allowed to stir under N$_2$ at 60° C. for 30 minutes. The solution is stirred at 60° C. under a sustained H$_2$ pressure of 60 psi for 22 hours. The reaction is cooled to ambient temperature where it is repeatedly purged with N$_2$. The crude MeOH solution of (5R)-7-[2-(4-fluorophenyl)-5-isopropyl-3-phenyl-4-phenylcarbamoyl-pyrrol-1-yl]-3,5-dihydroxy-heptanoic acid, methyl ester is carried on to subsequent steps without purification, or optionally, it can be isolated via flash column chromatography on silica gel, eluting with ethyl acetate-heptane mixtures. HPLC analysis (YMC ODS AQ S5; 1 mL/min; 30° C.; 254 nm: CH$_3$CN/H$_2$O, 60:40 (0–22 min.) to 100:0 (27–37 min.) to 60:40) indicated a syn:anti ratio of 1:1.4.

Chiral HPLC analysis (Chiralcel OD-H column; 5% EtOH:Hexanes; tR(3R,5R)=23.1 min./t$_R$(3R,5S)=18.0 min./t$_R$(3S,5S)=24.8 min./t$_R$(3S,5R)=19.9 min.) indicated an enantiomeric excess at C-5 of ≧97%, favoring the (R) configuration.

m/z (DCI(m+1)) 573; calcd for C$_{34}$H$_{37}$FN$_2$O$_5$ 572.27.

Step 7: 5-(4-Fluorophenyl)-2-isopropyl-1-[2-((S)-6-oxo-3,6-dihydro-2H-pyran-2-yl)-4-phenyl-1H-pyrrole-3-carboxylic acid phenylamide

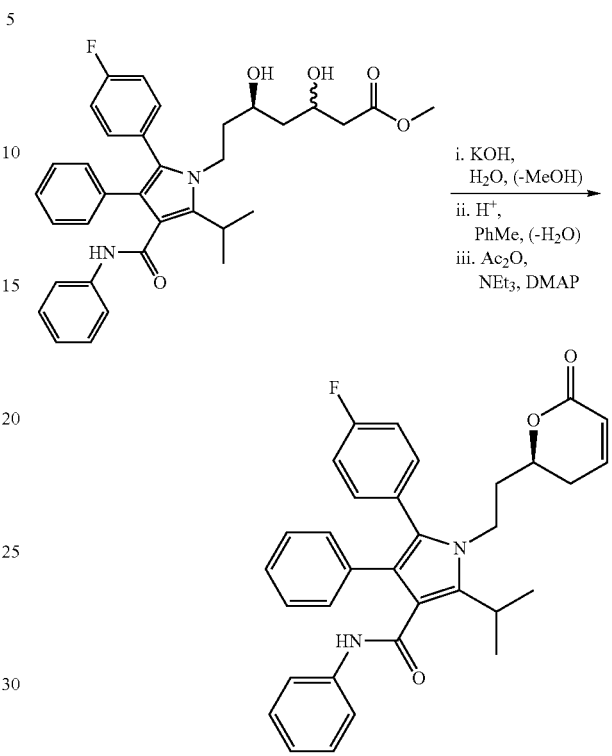

A suitable nitrogen inerted reactor is charged with KOH (110.0 mmol) and water (300 mL). To this rapidly stirring solution is added the crude Step 6 solution of (5R)-7-[2-(4-fluorophenyl)-5-isopropyl-3-phenyl-4-phenylcarbamoyl-pyrrol-1-yl]-3,5-dihydroxy-heptanoic acid, methyl ester (ca. 100 mmol/>98% ee) in MeOH (250 mL). The mixture is heated under a nitrogen atmosphere to an internal temperature of ca. 85° C. During this time, MeOH is removed via distillation. The resulting reaction mixture is allowed to cool to 45° C., where it is washed with MtBE (2×150 mL). The MtBE phases are separated and discarded. To the 45° C. aqueous phase is added toluene (125 mL), followed by a slow addition of 6N HCl (20 mL). The two-phase mixture is stirred for 10 minutes, and the layers are separated. The aqueous phase is extracted with a second portion of toluene (125 mL) and discarded. The combined organics are heated to reflux under a nitrogen atmosphere. During this time, 130 mL of distillate is collected and discarded. The resulting solution is cooled to ca. 60° C., where NEt$_3$ (140 mmol), DMAP (2.0 mmol) and Ac$_2$O (70.0 mmol) are added successively at such a rate as to maintain an internal reaction temperature of 55° C. to 65° C. This solution is stirred for ca. 1.5 hrs at 60° C. The mixture is cooled to 50° C., where 1N HCl (100 mL) is added slowly. The two-phase mixture is stirred for 10 minutes, the phases are separated, and the aqueous phase discarded. The organic phase is washed with second portions of 1N HCl (100 mL) and water (100 mL) while maintaining a temperature of 45° C. to 55° C. The toluene solution is diluted with Bu$_2$O (200 mL) and the resulting solution is slowly cooled to 0° C. with continuous agitation. The resulting solid is collected on a filter funnel and dried under vacuum to provide 5-(4-fluorophenyl)-2-isopropyl-1-[2-((S)-6-oxo-3,6-dihydro-2H-pyran-2-yl)-ethyl]-4-phenyl-1H-pyrrole-3-carboxylic acid phenylamide as a white to off-white solid (34.4 g). This material is carried on to subsequent steps without further purification, or optionally, it can be re-precipitated from IPA/H$_2$O.

m/z (DCI(m+1)) 523; calcd for C$_{33}$H$_{31}$FN$_2$O$_3$ 522.23.

Chiral HPLC analysis (Chiralpak AD column; 1 ml/min; 30° C.; 254 nm; 10% IPA:Hexanes; tR(R)=18 min./tR(S)=16 min.) indicated an enantiomeric excess of >98%, favoring the (R) configuration.

Step 8: 5-(4-Fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide Method A

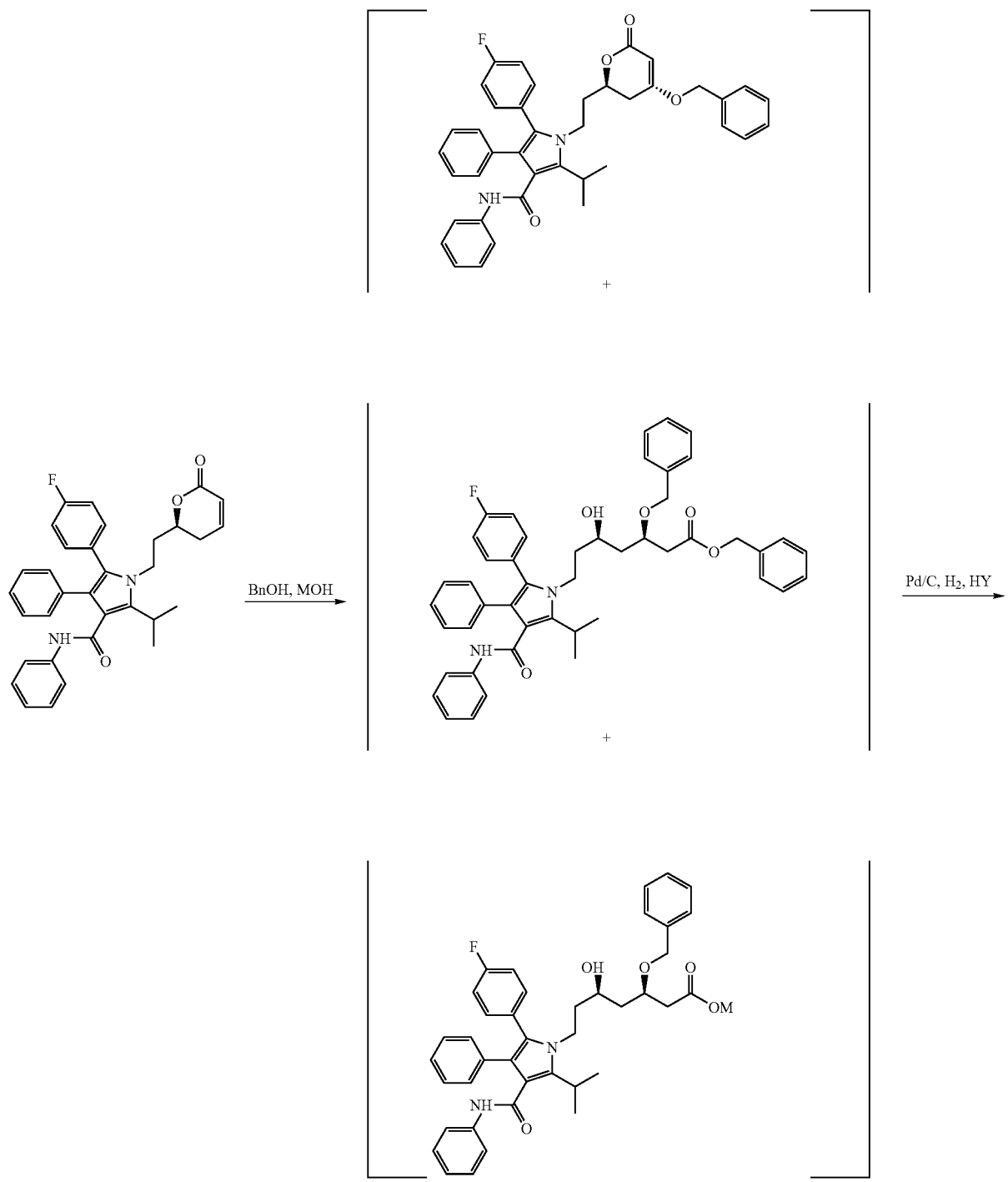

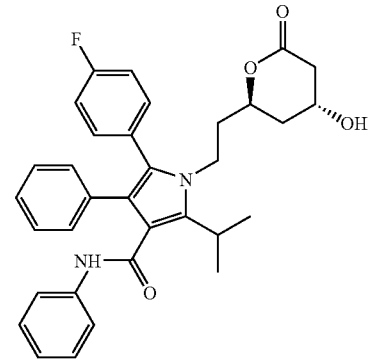

An argon-purged reactor is charged with 5-(4-fluorophenyl)-2-isopropyl-1-[2-((S)-6-oxo-3,6-dihydro-2H-pyran-2-yl)-ethyl]-4-phenyl-1H-pyrrole-3-carboxylic acid phenylamide (0.020 mol/>99% ee) and benzyl alcohol (52 mL). The reaction mixture is cooled to −10° C. and NaOH (0.040 mol) is added. After stirring for 19 hours at −10C the reaction is quenched with 37% HCl (0.042 mol) and diluted with water (25 mL) and toluene (25 mL). After the mixture is warmed to ambient temperature, the lower aqueous layer is discarded. The upper organic layer is combined with 20% Pd(OH)$_2$/C (1.0 g) and H$_2$SO$_4$ (0.01 moles) and hydrogenated under 50 psi hydrogen at 50° C. for 16 hours. The reaction mixture is heated to 80° C. and filtered through diatomaceous earth. The reactor and catalyst cake is rinsed with hot toluene (10 mL). The lower aqueous layer is discarded. The upper organic layer is washed with a warm solution of aqueous HCl (0.16 g 37% HCl in 25 mL hot water) and heated to reflux for 2.5 hours under argon, removing water azeotropically. The reaction mixture is cooled to 65° C. and seeded with 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide. After 2 hours the reaction mixture is allowed to slowly cool to ambient temperature. The resulting slurry is cooled to about 0° C. The product is collected and washed with cold toluene (25 mL). The resulting solid is dissolved in hot toluene (95 mL) and cooled to 65° C. and held for 2 hours.

The reaction mixture is slowly cooled to ambient temperature and further cooled to 0° C. The product is collected, washed with cold toluene (25 mL) and dried in vacuo at 70° C. overnight to afford 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide (8.4 g) as a white solid.

HPLC analysis (YMC ODS AQ S5; 1 mL/min; 30° C.; 254 nm: CH$_3$CN/H$_2$O, 60:40 (0–22 min.) to 100:0 (27–37 min.) to 60:40) indicated an anti:syn ratio of >99:1.

Chiral HPLC analysis (Chiralcel OF; 1 mL/min; 60° C.; 254 nm; 20%

IPA:Hexanes; $t_R$(3R,5R)=26 min./$t_R$(3R,5S)=59 min./$t_R$(3S,5S)=33 min./$t_R$(3S,5R)=37 min.) indicated an enantiomeric excess at C-5 of >99%, favoring the (R) configuration.

m/z (DCI(m+1)) 541; calcd for C$_{33}$H$_{33}$FN$_2$O$_4$ 540.24.

In a process analogous to Step 8 METHOD A, substituted benzylic alcohol derivatives (e.g., p-methoxy-benzyl alcohol) may be used in place of benzyl alcohol to afford the corresponding compounds.

Method B

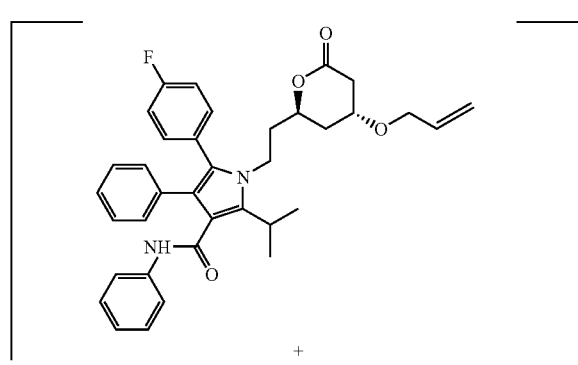

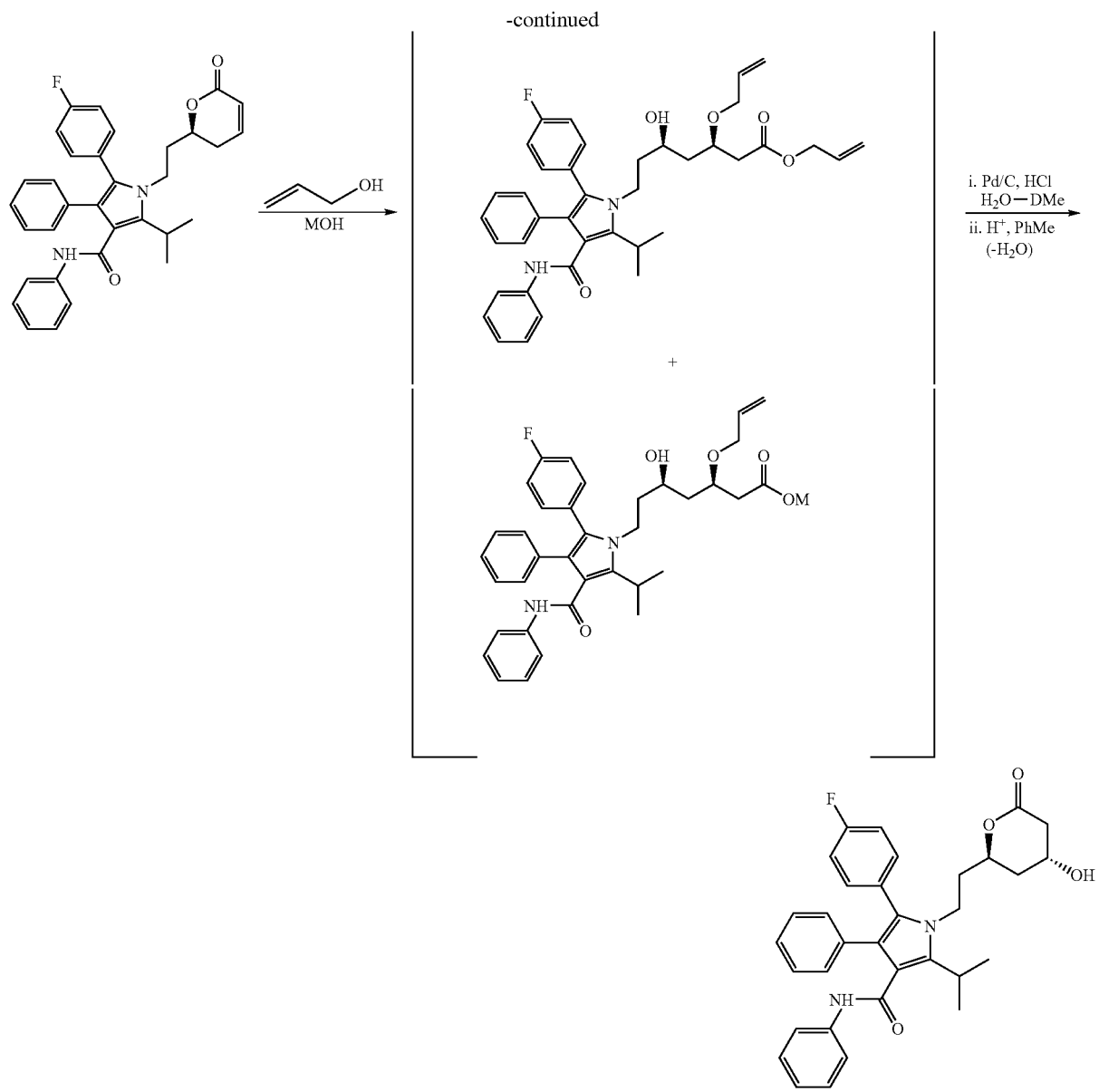

An argon-purged reactor is charged with 5-(4-fluorophenyl)-2-isopropyl-1-[2-((S)-6-oxo-3,6-dihydro-2H-pyran-2-yl)-ethyl]-4-phenyl-1H-pyrrole-3-carboxylic acid phenylamide (19.1 mmol/>99% ee) and allyl alcohol (50 mL). The reaction mixture is cooled to −5° C. and LiOH (38.2 mmol) is added. After stirring for 1 hour at −5° C. the reaction is quenched with 37% HCl (42 mmol) and toluene (125 mL). After the mixture is warmed to ambient temperature, the reaction is concentrated to a volume of ca. 75 mL. Additional toluene (50 mL) is added and the reaction is concentrated via distillation to a crude oil that solidifies upon standing. The crude residue is taken up in DME (340 mL). To this solution is added deionized water (20 mL), p-toluenesulfonic acid (2.25 g) and 5% Pd/C (11 g; 50% water-wet). The resulting mixture is heated to 45° C. under a $N_2$ atmosphere for 1.5 hours and at ambient temperature for an additional 16 hours. The solution is passed through filter aid to remove catalyst, and solvent is removed in vacuo. The residue is taken up in toluene (50 mL). Water (75 mL) and KOH (950 mg) are added, and the reaction mixture is heated to 65° C. where the layers are separated. The aqueous phase is washed with toluene (25 mL) at 65° C. and the combined toluene layers are discarded. To the aqueous phase is added toluene (50 mL), followed by 6N HCl (3.8 mL). The mixture is stirred vigorously at 65° C. for 5 minutes and the phases are separated. The toluene phase is heated to reflux for 2.5 hours under argon, removing water azeotropically. The reaction mixture is cooled to 65° C. and seeded with 5-(4-fluorophenyl)-1-[2-((2R,4R)-4-hydroxy-6-oxo-tetrahydro-pyran-2-yl)-ethyl]-2-isopropyl-4-phenyl-H-pyrrole-3-carboxylic acid phenylamide. After 2 hours the reaction mixture is allowed to slowly cool to ambient temperature. The resulting slurry is cooled to about 0° C. The product is collected and washed with cold toluene (25 mL). The resulting solid is dissolved in hot toluene (95 mL) and cooled to 65° C. and held for 2 hours. The reaction mixture is slowly cooled to ambient temperature and further cooled to 0° C. The product is collected, washed with cold toluene (25 mL) and dried in vacuo at 70° C. overnight to afford 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide as a white solid.

HPLC analysis (YMC ODS AQ S5; 1 ml/min; 30° C.; 254 nm: $CH_3CN/H_2O$, 60:40 (0–22 min) to 100:0 (27–37 min) to 60:40) indicated an anti:syn ratio of >99: 1.

Chiral HPLC analysis (ChiralCel OF; 1 mL/min; 60° C.; 254 nm; 20%

IPA:Hexanes; tR(3R,5R)=26 min./tR(3R,5S)=59 min. tR(3S,SS)=33 min./$t_R$(3S,5R)=37 min.) indicated an enantiomeric excess at C-5 of >99%, favoring the (R) configuration.

m/z (DCI(m+1)) 541; calcd for $C_{33}H_{33}FN_2O_4$ 540.24.

In a process analogous to Step 8 METHOD B, allylic alcohol derivatives (e.g., crotyl alcohol) may be used in place of allyl alcohol to afford the corresponding compounds.

Method C

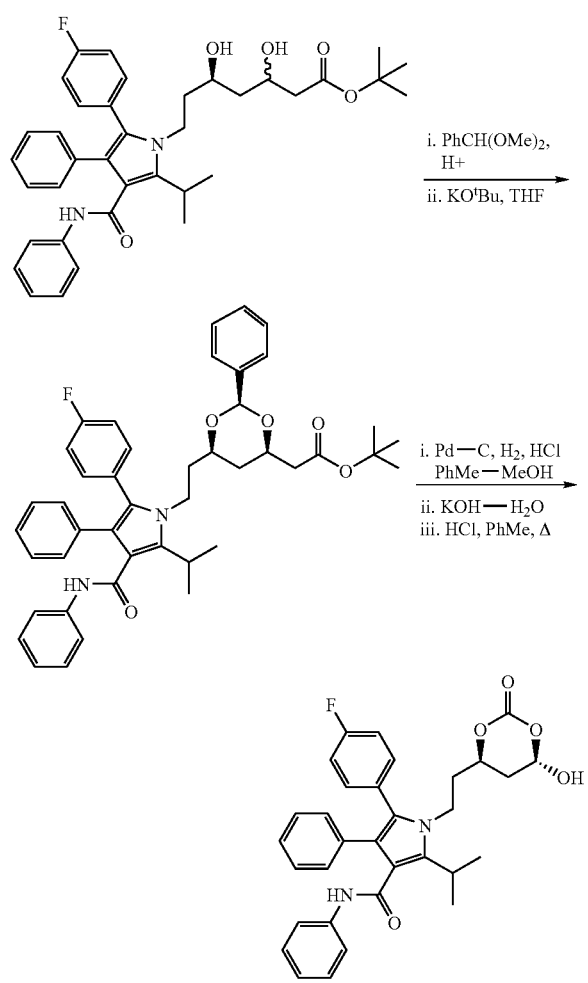

Operation A

A nitrogen inerted reactor is charged with (5R)-7-[2-(4-fluorophenyl)-5-isopropyl-3-phenyl-4-phenylcarbamoyl-pyrrol-1-yl]-3,5-dihydroxy-heptanoic acid, tert-butyl ester (10.0 mmol), benzaldehyde dimethyl acetal (44.0 mmol), toluene (40 mL) and p-toluenesulfonic acid monohydrate (1.0 mmol). The reaction is stirred vigorously under vacuum for ca. 20 hours, or until complete reaction as determined by analysis of an aliquot by HPLC. The solution is cooled under a nitrogen atmosphere to ca.–5° C. where a IM THF solution of KOtBu (9.0 mmol) is added in three equal portions, separated by 30 to 45 minutes. The resulting solution is allowed to stir an additional 12 to 14 hours at 0° C. The reaction is quenched by the slow addition of 1N HCl (10 mL). The resulting two-phase mixture is allowed to warm to ca. 15° C. and is transferred to a separatory funnel where the aqueous phase is removed and discarded. The organic phase is washed with saturated aqueous NaCl (100 mL), dried over anhydrous $MgSO_4$ (25 g), filtered and concentrated in vacuo to a crude oil. This material is carried on to subsequent steps without purification, or optionally, it can be re-precipitated from ether/hexanes.

m/z (APCI(m+1)) 703.4; calcd for $C_{44}H_{47}FN_2O_5$ 702.35.

In a process analogous to Step 8 METHOD C OPERATION A using the appropriate ester from Step 6 in place of (5R)-7-[2-(4-fluorophenyl)-5-isopropyl-3-phenyl-4-phenyl-carbamoyl-pyrrol-1-yl]-3,5-dihydroxy-heptanoic acid, tert-butyl ester, one obtains the following compounds, for example:

((4R,6R)-6-{2-[2-(4-fluorophenyl)-5-isopropyl-3-phenyl-4-phenylcarbamoyl-pyrrol-1-yl]-ethyl}-2-phenyl-[1,3]dioxan-4-yl)-acetic acid methyl ester.

((4R,6R)-6-{2-[2-(4-fluorophenyl)-5-isopropyl-3-phenyl-4-phenylcarbamoyl-pyrrol-1-yl]-ethyl}-2-phenyl-[1,3]dioxan-4-yl)-acetic acid ethyl ester.

((4R,6R)-6-{2-[2-(4-fluorophenyl)-5-isopropyl-3-phenyl-4-phenylcarbamoyl-pyrrol-1-yl]-ethyl}-2-phenyl-[1,3]dioxan-4-yl)-acetic acid isopropyl, ester.

Operation B

A nitrogen inerted pressure reactor is charged with ((4R,6R)-6-{2-[2-(4-fluorophenyl)-5-isopropyl-3-phenyl-4-phenylcarbamoyl-pyrrol-1-yl]-ethyl}-2-phenyl-[1,3]dioxan-4-yl)-acetic acid tert-butyl ester from OPERATION A (5.0 g), 5% Pd/C (0.45 g; 50% $H_2O$-wet), 2N HCl in MeOH (1.9 mL), toluene (11 mL), and MeOH (3.1 mL). The vessel and its contents are degassed via two cycles of partial evacuation and nitrogen pressurization (25 mm Hg and 50 psi, respectively). The atmosphere is switched to hydrogen via three cycles of partial evacuation and hydrogen pressurization (25 mm Hg and 50 psi, respectively). The reaction is stirred vigorously at 40° C. under a positive pressure of $H_2$ (ca. 50 psi) for ca. 2.5 hours. The reaction is allowed to cool to ambient temperature, and the hydrogen pressure is released and replaced with nitrogen. The reaction is passed through filtering agent to remove the catalyst, rinsing thoroughly with MeOH (2×5 mL). To this solution is added KOH (0.6 g) in water (25 mL). The reaction is stirred vigorously under a nitrogen atmosphere and heated to an internal reaction temperature of ca. 90° C., removing MeOH via distillation. The two-phase mixture is allowed to cool to 70° C. and the upper toluene phase is separated and discarded. The aqueous phase is washed with a second portion of toluene (10 mL) at 70° C. This organic wash is also separated and discarded. To the aqueous phase is added toluene (10 mL), followed by a slow addition of 2N HCl (5 mL). The two-phase mixture is stirred for 10 minutes and the layers are separated. The aqueous phase is extracted with a second portion of toluene (10 mL) and is discarded. The combined organics are heated to reflux under a Dean-Stark water trap for 2.5 hours under argon. The reaction mixture is cooled to 65° C. and seeded with 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide. After 2 hours the reaction mixture is allowed to slowly cool to ambient temperature. The resulting slurry is cooled to ca. 0° C. The product is collected and washed with cold toluene (5 mL). The resulting solid is dissolved in hot toluene (20 mL) and cooled to 65° C. and held for 2 hours. The reaction mixture is slowly cooled to ambient temperature and then to 0° C.

The product is collected, washed with cold toluene (5 μL) and dried in vacuo at 70° C. overnight to afford 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide as a white solid.

m/z (DCI(m+1)) 541; calcd for $C_{33}H_{33}FN_2O_4$ 540.24.

Method D

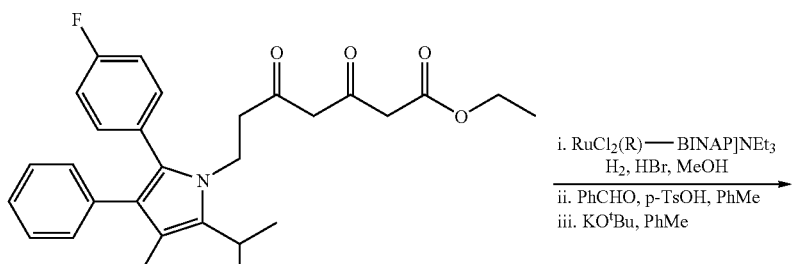

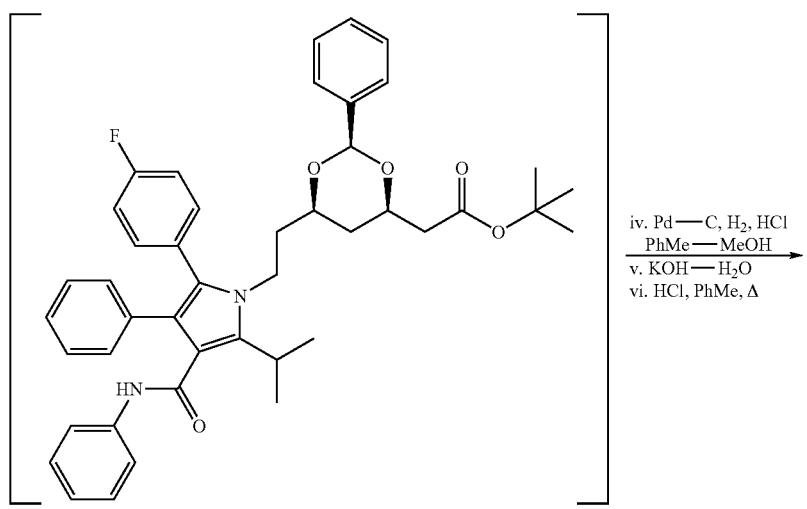

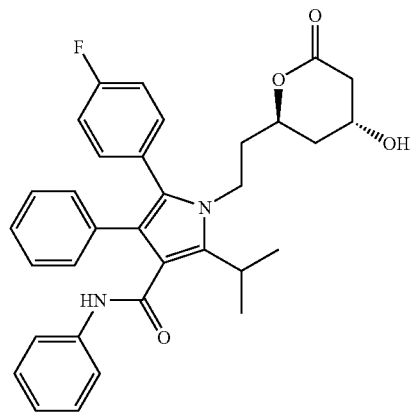

A nitrogen inerted pressure reactor is charged with 7-[2-(4-fluorophenyl)-5-isopropyl-3-phenyl-4-phenylcarbamoyl-pyrrol-1-yl]-3,5-dioxo-heptanoic acid, ethyl ester (100.0 mmol) and EtOH (250 μL). The resulting slurry is heated with stirring to ca. 55° C. to afford a homogeneous solution. The vessel and its contents are degassed via three 50 psi pressure purges with argon. Under a steady flow of argon, 1 M ethanolic HBr (7.0 mmol) and the RuCl$_2$([(R)-BINAP]NEt$_3$ catalyst (0.5 mmol) are added, and the reactor is given an additional 50 psi pressure purge with argon. The atmosphere is switched to hydrogen via three 50 psi pressure purges. The reaction is stirred vigorously at 65° C. under a sustained pressure of hydrogen (50 psi) until H$_2$ uptake ceases. The reaction is allowed to cool to ca. 50° C., where the hydrogen pressure is released and replaced with nitrogen. The crude EtOH solution of (5R)-7-[2-(4-fluorophenyl)-5-isopropyl-3-phenyl-4-phenylcarbamoyl-pyrrol-1-yl]-3,5-dihydroxy-heptanoic acid, methyl ester is diluted with toluene (250 mL). To this solution is added benzaldehyde (150 mmol) and p-TsOH monohydrate (5 mmol). The resulting reaction mixture is heated to a pot temperature of 110° C., removing EtOH and water via their toluene azeotropes. The solution is cooled under a nitrogen atmosphere to ca. −5° C. where a 1 M THF solution of KOtBu (90 mmol) is added in three equal portions, separated by 30 to 45 minutes. The resulting solution is allowed to stir an additional 12 to 14 hours at 0° C. The reaction is quenched by the slow addition of 1N HCl (100 mL). The resulting two-phase mixture is allowed to warm to ca. 15° C. and is transferred to a separatory funnel where the aqueous phase is removed and discarded. The organic phase is washed with saturated aqueous NaCl (25 mL), dried over anhydrous MgSO$_4$ (5 g), filtered and concentrated in vacuo to a crude oil that is taken up in MeOH (200 mL). This solution is transferred to a nitrogen inerted pressure reactor containing 5% Pd/C (5 g; 50% water-wet). Concentrated HCl (2 mL) is added and the reaction is stirred under a sustained pressure of H$_2$ (50 psi) for ca. 3 hours at 50° C. The reaction mixture is cooled to ambient temperature, the H$_2$ is replaced by N$_2$, and the catalyst is removed via filtration. This solution of (3R,5R)-7-[2-(4-fluorophenyl)-5-isopropyl-3-phenyl-4-phenylcarbamoyl-pyrrol-1-yl]-3,5-dihydroxy-heptanoic acid, methyl ester is transferred to a nitrogen inerted reactor charged with KOH (110.0 mmol) and water (300 mL). The mixture is heated under a nitrogen atmosphere to an internal temperature of ca. 85° C. During this time, MeOH is removed via distillation. The resulting reaction mixture is allowed to cool to 45° C., where it is washed with MtBE (2×150 mL). The MtBE phases are separated and discarded. To the 45° C. aqueous phase is added toluene (125 mL), followed by a slow addition of 6N HCl (20 mL). The two-phase mixture is stirred for 10 minutes and the layers are separated. The aqueous phase is extracted with a second portion of toluene (125 mL) and is discarded. The combined organics are heated to reflux under a Dean-Stark water trap for 2.5 hours under argon. The reaction mixture is cooled to 65° C. and seeded with 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide. After 2 hours the reaction mixture is allowed to slowly cool to ambient temperature. The resulting slurry is cooled to ca. 0° C. The product is collected and washed with cold toluene (100 mL). The resulting solid is dissolved in hot toluene (350 mL) and cooled to 65° C. where it is held for 2 hours. The reaction mixture is slowly cooled to ambient temperature and then to 0° C. The product is collected, washed with cold toluene (100 ML) and dried in vacuo at 70° C. to afford 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide as a white solid.

m/z (DCI(m+1)) 541; calcd for C$_{33}$H$_{33}$FN$_2$O$_4$ 540.24.

Step 9: (R,R)-7-[2-(4-Fluorophenyl)-5-isopropyl-3-phenyl-4-phenylcarbamoyl-pyrrol-1-yl]-3,5-dihydroxy-heptanoic acid, calcium salt

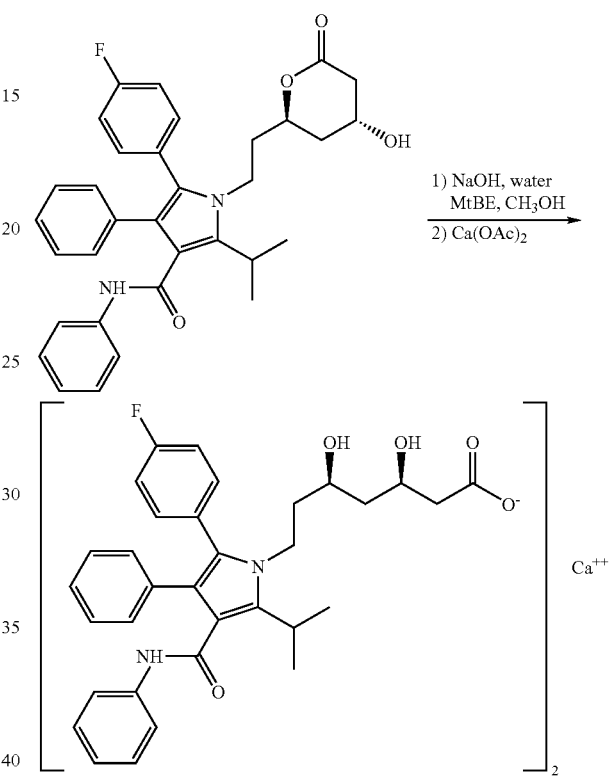

An argon-purged reactor is charged with 5-(4-fluorophenyl)-1-[2-((2R,4R)-4-hydroxy-6-oxo-tetrahydro-pyran-2-yl)-ethyl]-2-isopropyl-4-phenyl-1H-pyrrole-3-carboxylic acid phenylamide (14.8 mmol), MtBE (45 mL) and MeOH (20 mL). A solution of NaOH (15.2 mmol) in water (103 mL) is added and the reaction mixture heated to 52° C. After heating for ca. 1 hour, the reaction mixture is cooled to 34° C. and the layers are allowed to separate. The upper organic layer is discarded. The lower aqueous layer is washed with MtBE (33 mL) at ca. 33° C. The lower aqueous layer is diluted with MtBE (2 mL) and heated to 52° C. under argon. A warm solution of Ca(OAc)$_2$.H$_2$O (7.5 mmol) in water (44 mL) is added over ca. 2 hours. About 5 minutes after the start of the Ca(OAc)$_2$ addition, the reaction mixture is seeded with a slurry of (R,R)-7-[2-(4-fluorophenyl)-5-isopropyl-3-phenyl-4-phenylcarbamoyl-pyrrol-1-yl]-3,5-dihydroxy-heptanoic acid, calcium salt (0.08 mmol) in water (1.2 mL) and methanol (0.4 mL). After the Ca(OAc)$_2$ addition is complete, the reaction mixture is held for ca. 15 minutes at 52° C. and cooled to 20° C. The product is collected, washed sequentially with a 2:1 solution of aqueous methanol (48 mL) and water (49 mL). After drying in vacuo at 70° C., (R,R)-7-[2-(4-fluorophenyl)-5-isopropyl-3-phenyl-4-phenylcarbamoyl-pyrrol-1-yl]-3,5-dihydroxy-heptanoic acid, calcium salt (8.7 g) is obtained as a white solid. The analytical specifications of this material are in agreement with the values reported in the prior art.

Preparation of Catalysts

EXAMPLE A

RuCl?(DMF)$_n$[(R)-(+)-Cl—MeO-BIPHEP1 complex

A suitable reaction flask is charged with DMF (17.5 nL). The vessel and its contents are degassed via two cycles of partial evacuation and nitrogen pressurization (25 mm Hg and 10 psi, respectively). The excess nitrogen pressure is released, and benzene ruthenium(II) chloride dimer (0.50 mmol) and (R)-(+)-Cl—MeO-BIPHEP (1.10 mmol) are added in rapid succession. The vessel and its contents are again degassed via two cycles of partial evacuation and nitrogen pressurization (25 mm Hg and 10 psi, respectively). The excess nitrogen pressure is released, and the reactor is heated to ca. 100° C. for 10 minutes. The resulting solution is allowed to cool to <50° C. where solvent is removed in vacuo, affording RuCl2(DMF)$_n$[(R)-(+)-Cl—MeO-BI-PHEP] as a rusty-brown solid. The crude complex is used directly in subsequent reactions without purification or unambiguous characterization, or optionally, can be stored under an inert atmosphere for future use.

In a process analogous to EXAMPLE A using the appropriate chiral diphosphine ligand in place of (R)-(+)-Cl—MeO-BIPHEP, the following complexes can be obtained, for example:

RuCl$_2$(DMF)$_n$[(R)-(+)-BINAP]$_n$ complex.
RuCl2(DMF)$_n$[(R)-(+)-pTol-BINAP]$_n$ complex.
RuCl$_2$(DMF)$_n$[(R)-(+)—C4-TunaPhos]$_n$ complex.
RuCl$_2$(DMF)$_n$[(R)-(+)—C2-TunaPhos]$_n$ complex.
RuCl$_2$(DMF)$_n$[(S)-(−)-MeO-BIPHEP]$_n$ complex.

EXAMPLE B

RuCl$_2$[(R)-(+)-BINAP] (NEt3 n complex

A nitrogen inerted pressure reactor is charged with dichloro-(1,5-cyclooctadiene)-ruthenium (II) dimer (0.15 mmol) and (R)-(+)-BINAP (0.32 mmol). Toluene (8.0 mL) is added, followed by triethylamine (4.5 mmol). The vessel and its contents are degassed via two cycles of partial evacuation and nitrogen pressurization (25 mm Hg and 10 psi, respectively). The excess nitrogen pressure is released, and the reactor is sealed and heated to ca. 140° C. where it is maintained for ca. 4 hours. The resulting clear red solution is allowed to cool to ≦40° C. where solvent is removed in vacuo, affording RuCl$_2$[(R)-(+)-BINAP] (NEt3)$_n$ complex as a rusty-brown solid. The crude complex is used directly in subsequent reactions without purification or unambiguous characterization, or optionally, can be stored under an inert atmosphere for future use.

In a process analogous to EXAMPLE B using the appropriate chiral diphosphine ligand in place of (R)-(+)-BINAP, the following complexes can be obtained, for example:

RuCl$_2$[(R)-(+)-Cl—MeO-BIPHEP] (NEt3)$_n$ complex.
RuCl$_2$[(R)-(+)-BINAP] (NEt3)$_n$ complex.
RuCl$_2$[(R)-(+)-pTol-BINAP] (NEt3)$_n$ complex.

EXAMPLE C

[Ru(TFA)$_2$((R)-(+)-Cl—MeO-BIPHEP)]$_n$ complex

A suitable reaction flask is charged with acetone (50 mL). The vessel and its contents are degassed via two cycles of partial evacuation and argon pressurization (25 mm Hg and 10 psi, respectively). The excess argon pressure is released, and (0.50 mmol) and (R)-(+)-Cl—MeO-BIPHEP (0.51 mmol) are added in rapid succession. The vessel and its contents are again degassed via two cycles of partial evacuation and argon pressurization (25 mm Hg and 10 psi, respectively). The excess argon pressure is released, and the reactor is stirred vigorously at ca. 30° C. Trifluoroacetic acid (1.2 mmol) is added via syringe and the reaction mixture is stirred for an additional 1-hour period. Solvent is removed in vacuo, with careful omission of O$_2$, to afford [Ru(TFA)$_2$((R)-(+)-Cl—MeO-BIPHEP)]$_n$ complex as a solid. The crude complex is used directly in subsequent reactions without purification or unambiguous characterization, or optionally, can be stored under an inert atmosphere for future use.

In a process analogous to EXAMPLE C using the appropriate chiral diphosphine ligand in place of (R)-(+)-Cl—MeO-BIPHEP, the following complexes can be obtained, for example:

[Ru(TFA)$_2$((R)-(+)-MeO-BIPHEP)]$_n$ complex.
[Ru(TFA)$_2$((R)-(+)-BINAP)]$_n$ complex.
[Ru(TFA)$_2$((R)-(+)-pTol-BINAP)]$_n$ complex.

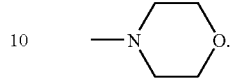

What is claimed is:

1. A compound of Formula (8)

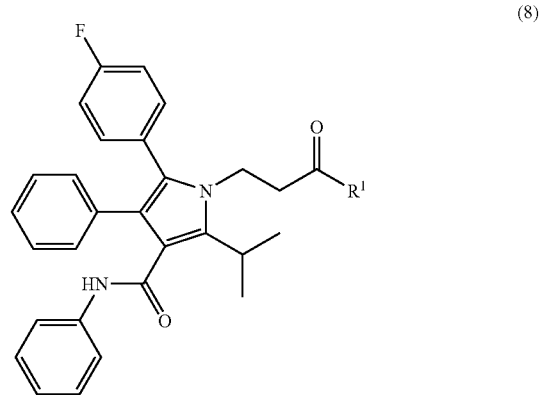

(8)

wherein R$^1$ is -XR wherein
X is O,
S, or
Se, or R$^1$ is

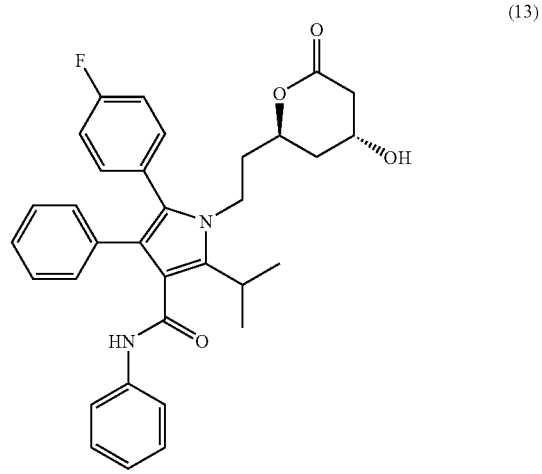

(13)

wherein $R^2$ or $R^3$ is independently
alkyl,
cycloalkyl,
arylalkyl, or
aryl or
$R^2$ and $R^3$ together are
—$(CH_2)_4$—,
—$(CH_2)_5$—,
—$(CH(R^4)$—$CH_2)_3$—,
—$(CH(R^4)$—$CH_2)_4$—,
—$(CH(R^4)$—$(CH_2)_2$—$CH(R^4))$—,
—$(CH(R^4)$—$(CH_2)_3$—$CH(R^4))$—,
—$CH_2$—$CH_2$—A—$CH_2$—$CH_2$—,
—$CH(R^4)$—$CH_2$—A—$CH_2CH_2$—,
—$CH(R^4)$—$CH_2$—A—$CH_2$—$CH(R^4)$—
wherein $R^4$ is alkyl of from one to four carbon atoms, A is O, S, or N, and R is alkyl, aryl, arylailcyl, or heteroaryl.

2. The compound according to claim 1, wherein $R^1$ is